(12) United States Patent
Itu et al.

(10) Patent No.: US 9,918,690 B2
(45) Date of Patent: *Mar. 20, 2018

(54) SYNTHETIC DATA-DRIVEN HEMODYNAMIC DETERMINATION IN MEDICAL IMAGING

(71) Applicant: Siemens Healthcare GmbH, Erlangen (DE)

(72) Inventors: Lucian Mihai Itu, Brasov (RO); Tiziano Passerini, Plainsboro, NJ (US); Saikiran Rapaka, Pennington, NJ (US); Puneet Sharma, Monmouth Junction, NJ (US); Chris Schwemmer, Forchheim (DE); Max Schoebinger, Hirschaid (DE); Thomas Redel, Poxdorf (DE); Dorin Comaniciu, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 9 days.

This patent is subject to a terminal disclaimer.

(21) Appl. No.: 14/876,852

(22) Filed: Oct. 7, 2015

(65) Prior Publication Data

US 2016/0148372 A1 May 26, 2016

Related U.S. Application Data

(63) Continuation of application No. 14/804,609, filed on Jul. 21, 2015, now Pat. No. 9,349,178.
(Continued)

(51) Int. Cl.
*G06K 9/00* (2006.01)
*A61B 6/00* (2006.01)
(Continued)

(52) U.S. Cl.
CPC ............ *A61B 6/5217* (2013.01); *A61B 5/026* (2013.01); *A61B 5/7267* (2013.01); *A61B 6/032* (2013.01);
(Continued)

(58) Field of Classification Search
CPC ...... G06F 19/12; G06F 19/24; G06F 19/3437; G06T 2207/20081; G06T 7/0012;
(Continued)

(56) References Cited

U.S. PATENT DOCUMENTS

| 8,805,051 B2 * | 8/2014 | Najarian | A61B 5/02007 382/128 |
| 8,821,408 B2 * | 9/2014 | Hu | A61B 5/02028 600/300 |

(Continued)

FOREIGN PATENT DOCUMENTS

WO 2014072861 5/2015

OTHER PUBLICATIONS

Asadi, Hamed, et al. "Machine learning for outcome prediction of acute ischemic stroke post intra-arterial therapy." PloS one 9.2 (2014): e88225.*
(Continued)

*Primary Examiner* — Jonathan S Lee

(57) ABSTRACT

In hemodynamic determination in medical imaging, the classifier is trained from synthetic data rather than relying on training data from other patients. A computer model (in silico) may be perturbed in many different ways to generate many different examples. The flow is calculated for each resulting example. A bench model (in vitro) may similarly be altered in many different ways. The flow is measured for each resulting example. The machine-learnt classifier uses features from medical scan data for a particular patient to estimate the blood flow based on mapping of features to flow
(Continued)

learned from the synthetic data. Perturbations or alterations may account for therapy so that the machine-trained classifier may estimate the results of therapeutically altering a patient-specific input feature. Uncertainty may be handled by training the classifier to predict a distribution of possibilities given uncertain input distribution. Combinations of one or more of uncertainty, use of synthetic training data, and therapy prediction may be provided.

23 Claims, 25 Drawing Sheets

Related U.S. Application Data

(60) Provisional application No. 62/083,373, filed on Nov. 24, 2014.

(51) Int. Cl.

| | | |
|---|---|---|
| G06T 7/00 | (2017.01) | |
| G06K 9/52 | (2006.01) | |
| G06K 9/62 | (2006.01) | |
| A61B 5/026 | (2006.01) | |
| G06F 19/00 | (2018.01) | |
| A61B 8/06 | (2006.01) | |
| A61B 8/08 | (2006.01) | |
| G06T 7/11 | (2017.01) | |
| A61B 6/03 | (2006.01) | |
| A61B 5/02 | (2006.01) | |
| A61B 5/00 | (2006.01) | |
| A61B 8/00 | (2006.01) | |

(52) U.S. Cl.
CPC .............. *A61B 6/504* (2013.01); *A61B 6/507* (2013.01); *A61B 8/06* (2013.01); *A61B 8/065* (2013.01); *A61B 8/5223* (2013.01); *G06F 19/3437* (2013.01); *G06K 9/52* (2013.01); *G06K 9/6201* (2013.01); *G06K 9/627* (2013.01); *G06K 9/6262* (2013.01); *G06T 7/0012* (2013.01); *G06T 7/11* (2017.01); *A61B 5/02007* (2013.01); *A61B 5/02028* (2013.01); *A61B 5/0263* (2013.01); *A61B 5/743* (2013.01); *A61B 6/469* (2013.01); *A61B 8/469* (2013.01); *A61B 2576/00* (2013.01); *G06F 19/321* (2013.01); *G06T 2200/04* (2013.01); *G06T 2207/10072* (2013.01); *G06T 2207/10076* (2013.01); *G06T 2207/20081* (2013.01); *G06T 2207/30101* (2013.01); *G06T 2207/30104* (2013.01)

(58) Field of Classification Search
CPC ....... A61B 5/026; A61B 5/7267; A61B 6/504; A61B 6/507; A61B 6/5217; A61B 8/06; A61B 8/065; A61B 8/5223; A61B 5/02007; A61B 5/02028; G06K 9/52; G06K 9/6201; G06K 9/627

See application file for complete search history.

(56) References Cited

U.S. PATENT DOCUMENTS

| | | | | |
|---|---|---|---|---|
| 9,087,147 | B1* | 7/2015 | Fonte | A61B 5/7275 |
| 9,092,743 | B2* | 7/2015 | Singer | A61B 5/7275 |
| 2012/0022384 | A1* | 1/2012 | Teixeira | A61B 5/0205 |
| | | | | 600/509 |
| 2012/0041321 | A1† | 2/2012 | Taylor | |
| 2012/0041739 | A1 | 2/2012 | Taylor | |
| 2012/0232853 | A1 | 9/2012 | Voigt et al. | |
| 2012/0330629 | A1* | 12/2012 | Prabhakarpandian | G01N 33/54346 |
| | | | | 703/2 |
| 2013/0041683 | A1* | 2/2013 | Boissel | G06F 19/12 |
| | | | | 705/2 |
| 2014/0073976 | A1† | 3/2014 | Fonte | |
| 2014/0073977 | A1 | 3/2014 | Grady et al. | |
| 2014/0114184 | A1 | 4/2014 | Klaiman et al. | |
| 2014/0249784 | A1 | 9/2014 | Sankaran et al. | |
| 2015/0042646 | A1 | 2/2015 | Comaniciu et al. | |
| 2015/0112182 | A1 | 4/2015 | Sharma | |
| 2015/0112901 | A1 | 4/2015 | Singer | |
| 2015/0242589 | A1 | 8/2015 | Neumann et al. | |
| 2015/0282765 | A1* | 10/2015 | Goshen | A61B 6/032 |
| | | | | 600/408 |
| 2015/0302139 | A1 | 10/2015 | Sankaran et al. | |
| 2016/0042144 | A1 | 2/2016 | Sankaran et al. | |
| 2016/0042145 | A1 | 2/2016 | Sankaran et al. | |

OTHER PUBLICATIONS

J. A. Goldstein et al., "The CT-STAT (Coronary Computed Tomographic Angiography for Systematic Triage of Acute Chest Pain Patients to Treatment) Trial," Journal of the American College of Cardiology, vol. 58, No. 14, pp. 1414-1422, 20110.

U. Hoffmann, M.D., et al., "Coronary CT Angiography versus Standard Evaluation in Acute Chest Pain," The New England Journal of Medicine, vol. 367, No. 4, pp. 299-308, 2012.

B-K Koo, M.D. et al., "Diagnosis of Ischemia-Causing Coronary Stenoses by Noninvasive Fractional Flow Reserve Computed From Coronary Computed Tomographic Angiograms," Journal of the American College of Cardiology, vol. 58, No. 19, pp. 1989-1997, 2011.

J. K. Min et al.., "Diagnostic Accuracy of Fractional Flow Reserve From Anatomic CT Angiography," JAMA, 308(12), pp. E1-E9, 2012.

P. D. Morris et al., "Virtual Fractional Flow Reserve From Coronary Angiography: Modeling the Significance of Coronary Lesions," JACC: Cardiovascular Interventions, vol. 6, No. 2, pp. 149-157, 2013.

B. L. Norgaard, M.D. et al., "Diagnostic performance of non-invasive fractional flow reserve derived from coronary CT angiography in suspected coronary artery disease: The NXT trial," JAAC, pp. 1-32, 2013.

R. Petraco, M.D. et al., "Hybrid iFR-FFR decision-making strategy: implications for enhancing universal adoption of physiology-guided coronary revascularisation," EuroIntervention, pp. 1-9, 2012.

M Renker, M.D. et al., "Comparison of Diagnostic Value of a Novel Non-Invasive Coronary Computed Tomography Angiography Method versus Standard Coronary Angiography for Assessing Fractional Flow Reserve," The American Journal of Cardiology, pp. 1-23, 2014.

M. I. Papafaklis, M.D. et al., "Fast virtual functional assessment of intermediate coronary lesions using routine angiographic data and blood flow simulation in humans: comparison with pressure wire—fractional flow reserve," EuroIntervention, pp. 1-14, 2014.

P. A. L. Tonino, M.D. et al., "Fractional Flow Reserve versus Angiography for Guiding Percutaneous Coronary Intervention," The New England Journal of Medicine, vol. 360, No. 3, pp. 213-224, 2009.

S. Tu, PhD et al., "Fractional Flow Reserve Calculation From 3-Dimensional Quantitative Coronary Angiography and TIMI Frame Count," JACC: Cardiovasular Interventions, vol. 7, No. 7, pp. 768-777, 2014.

Y. E. Yoon et al., "Noninvasive Diagnosis of Ischemia-Causing Coronary Stenosis Using CT Angiography," JACC: Cardiovascular Imaging, vol. 5, No. 11, pp. 1088-1096, 2012.

P. Sharma et al., System and Method for Mapping Patient Data from One Physiological State to Another Physiological State, patent pending, 2014.

J. Endres et al., "A Workflow for Patient-Individualized Virtual Angiogram Generation Based on CFD Simulation," Computational and Mathematical Methods in Medicine, vol. 2012, pp. 1-25.

(56) References Cited

OTHER PUBLICATIONS

G. M. Hutchins et al., "Vessel Caliber and Branch-Angle of Human Coronary Artery Branch-Points," Circulation Research, vol. 38, pp. 571-576, 1976.

G. S. Kassab et al., "Morphometry of pig coronary arterial trees," Am J Physiol., vol. 265, pp. H350-H365, 1993.

G. S. Kassab et al., "The Pattern of Coronary Arteriolar Bifurcations and the Uniform Shear Hypothesis," Annals of Biomechanical Engineering, vol. 23, pp. 13-20, 1995.

Z. Keshavarz-Motamed et al., "A new approach for the evaluation of the severity of coarctation of the aorta using Doppler velocity index and effective orifice area: In vitro validation and clinical implications," Journal of Biomechanics, vol. 45, pp. 1239-1245, 2012.

K. McLeod et al., "Atlas-Based Reduced Models of Blood Flows for Fast Patient-Specific Simulations," Statistical Atlases and Computational Models of the Heart, Lecture Notes in Computer Science vol. 6364, pp. 95-104, 2010.

C. D. Murray, "The Physiological Principle of Minimum Work: I. The Vascular System and the Cost of Blood Volume," Proc. of the National Academy of Sciences of the USA, vol. 12, pp. 207-214, 1926.

J. P. Mynard, "Computer Modelling and Wave Intensity Analysis of Perinatal Cardiovascular Function and Dysfunction," PhD Thesis, University of Melbourne, Australia, pp. 1-358, 2011.

M. Schrijver, "Angiographic Image Analysis to Assess the Severity of Coronary Stenoses," PhD thesis, University of Twente, pp. 1-241, 2002.

E. Soudah et al., "Validation of numerical flow simulations against in vitro phantom measurements in different type B aortic dissection scenarios," Comput Methods Biomech Biomed Engin., pp. 1-12, 2013.

C. A. Taylor et al., "Image-Based Modeling of Blood Flow and Vessel Wall Dynamics: Applications, Methods and Future Directions," Annals of Biomedical Engineering, vol. 38, pp. 1188-1203, 2010.

H. Thompson et al., "Indicator Transit Time Considered as a Gamma Variate," Circ Res., vol. 14, pp. 502-515, 1964.

H. B. Uylings, "Optimization of Diameters and Bifurcation Angles in Lung and Vascular Tree Structures," Bulletin of Mathematical Biology, vol. 39, pp. 509-520, 1977.

A. C. Van Der Wal, "Coronary artery pathology," Heart, vol. 93, pp. 1484-1489, 2007.

K. Veress et al., "Parameter estimation of flow-measurement in digital angiography," Journal Acta Cybernetica, vol. 20, pp. 189-206, 2011.

\* cited by examiner
† cited by third party

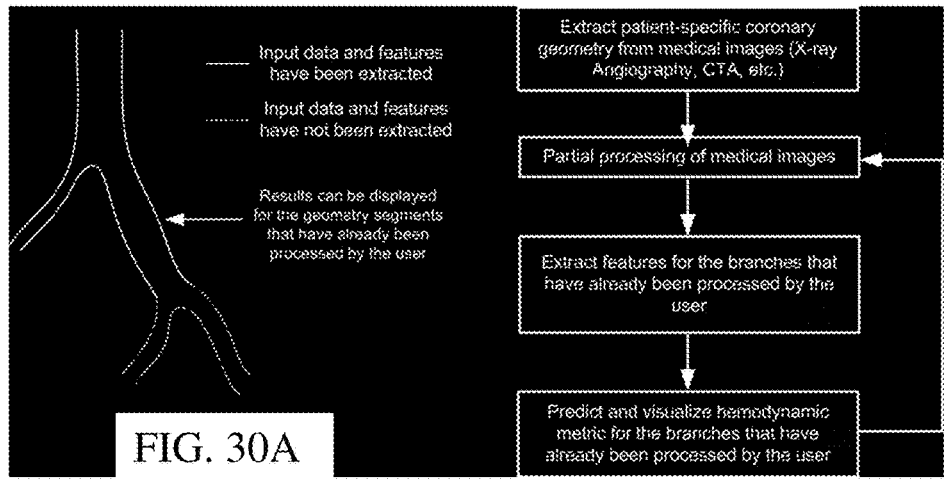
FIG. 30A
FIG. 30B
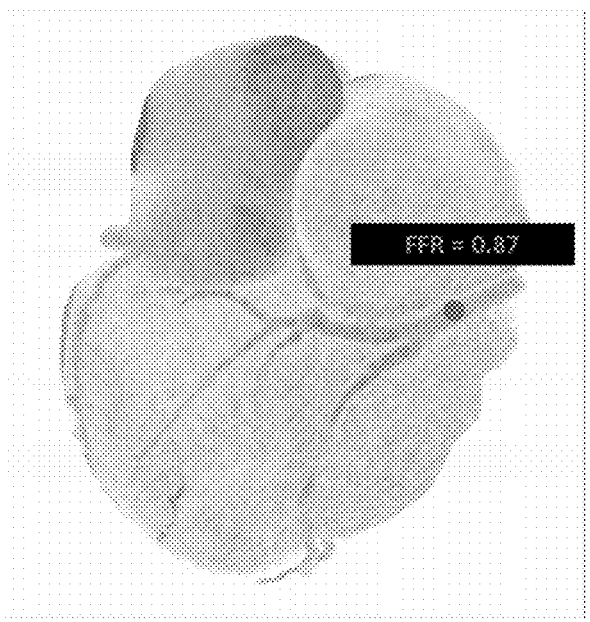
FIG. 31

SYNTHETIC DATA-DRIVEN HEMODYNAMIC DETERMINATION IN MEDICAL IMAGING

RELATED APPLICATIONS

The present patent document is a continuation application of U.S. Ser. No. 14/804,609, filed Jul. 21, 2015, which claims the benefit of the filing date under 35 U.S.C. § 119(e) of Provisional U.S. Patent Application Ser. No. 62/083,373, filed Nov. 24, 2014, which are hereby incorporated by reference.

BACKGROUND

The present embodiments relate to computation of blood flow in a vessel of a patient. In particular, a hemodynamic metric is estimated from non-invasive medical imaging data.

To estimate a value for flow, a computer model of the vessel is used. For flow in a particular patient, an anatomical model is fit to imaging data for that patient. Computational fluid dynamics estimates the flow from this patient-specific model. However, this approach relies only on geometrical information available from the medical imaging data.

In other approaches, machine learning is used. Either medical images or geometric models extracted from imaging data populate the training database. Features are extracted from these examples for training. The ground truth blood flow measurements are from the patient or computational fluid dynamics measurements. Machine training is performed to create a classifier able to estimate the blood flow from the input features. Due to reliance of patient-specific information, the machine learning may be limited. The training data should include as many examples as possible, such as hundreds or thousands of examples. Given the broad variability in the patient population, an even greater number of examples should be gathered for training. The availability of such examples is limited. The cost and time to gather sufficient training data is a detriment and outlier conditions are less likely to be accounted for in the machine-learnt classifier.

BRIEF SUMMARY

By way of introduction, the preferred embodiments described below include methods, computer readable media and systems for hemodynamic determination in medical imaging. Rather than relying on training data from other patients, the classifier is trained from synthetic data. A computer model (in silico) may be perturbed in many different ways to generate many different examples. The flow is calculated for each resulting example. A bench model (in vitro) may similarly be altered in many different ways. The flow is measured for each resulting example. The machine-learnt classifier uses features from medical scan data for a particular patient to estimate the blood flow based on mapping of features to flow learned from the synthetic data. Perturbations or alterations may account for therapy so that the machine-trained classifier may estimate the results of therapeutically altering a patient-specific input feature. Uncertainty may be handled by training the classifier to predict a distribution of possibilities given uncertain input distribution. Combinations of one or more of uncertainty, use of synthetic training data, and therapy prediction may be provided.

In a first aspect, a method is provided for hemodynamic determination in medical imaging. Medical scan data representing a vessel structure of a patient is acquired. A set of features are extracted from the medical scan data. A processor inputs the features to a machine-trained classifier. The machine trained classifier is trained only from synthetic data not specific to any patients. The processor outputs, with application of the machine-trained classifier to the features, a hemodynamic metric.

In a second aspect, a method is provided for hemodynamic determination in medical imaging. A plurality of examples of vessel arrangements are generated with computer modeling, physical modeling, or both computer and physical modeling. A value for a flow characteristic for each of the examples of the vessel arrangements is stored. With machine learning, a classifier is trained for predicting the flow characteristics for different vessel arrangements.

In a third aspect, a system is provided for hemodynamic determination in medical imaging. A scanner is configured to scan a vessel of a patient. A memory is configured to store a plurality of features of the vessel of the patient. The features are determined from the scan of the vessel. A processor is configured to apply the features to a machine-trained predictor trained with training data of synthetic examples of vessels, and to output a prediction of a value of a hemodynamic variable based on the application of the features to the machine-trained predictor. A display is configured to indicate the value of the hemodynamic variable.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIGS. 30A and 30B show one embodiment of regular or continuous computation of a hemodynamic metric while processing;

FIG. 31 is an example display of a hemodynamic value at a user selected location;

DETAILED DESCRIPTION OF THE DRAWINGS AND PRESENTLY PREFERRED EMBODIMENTS

Figure 1:
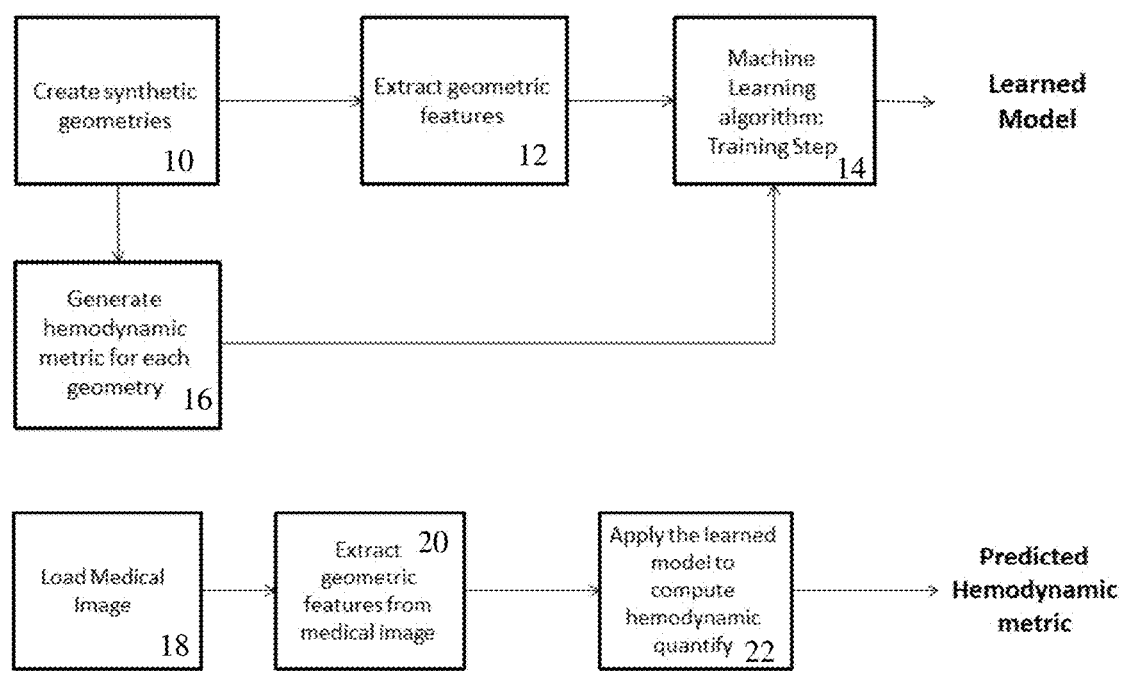
FIG. 1 is a flow chart diagram of one embodiment of a method for hemodynamic determination in medical imaging.

A data-driven approach provides for hemodynamics computation. The approach includes a machine-training phase and a prediction phase represented in FIG. 1. The training phase is an offline process, during which a database of synthetically generated geometries with corresponding hemodynamic metrics is first assembled in acts 12 and 16. In this database, a number of features that characterize the geometry or other characteristics represent each sample. These features are extracted in act 12. The mapping between the features and the hemodynamic metric is learnt in act 14 using a machine-learning based algorithm.

The prediction phase is an online process. The data for a specific patient is loaded in act 18. The required features are extracted from the new patient dataset in act 20. The values of the features are then used as an input to the pre-learned model. The machine-learnt classifier computes the value of the hemodynamic metric for new patient data (e.g., unseen data) in act 22. The learned mapping from the training phase is applied to the patient data. The machine-learnt computation of patient-specific hemodynamic metrics uses patient-specific geometrical features despite being trained on synthetic data.

Figure 2:
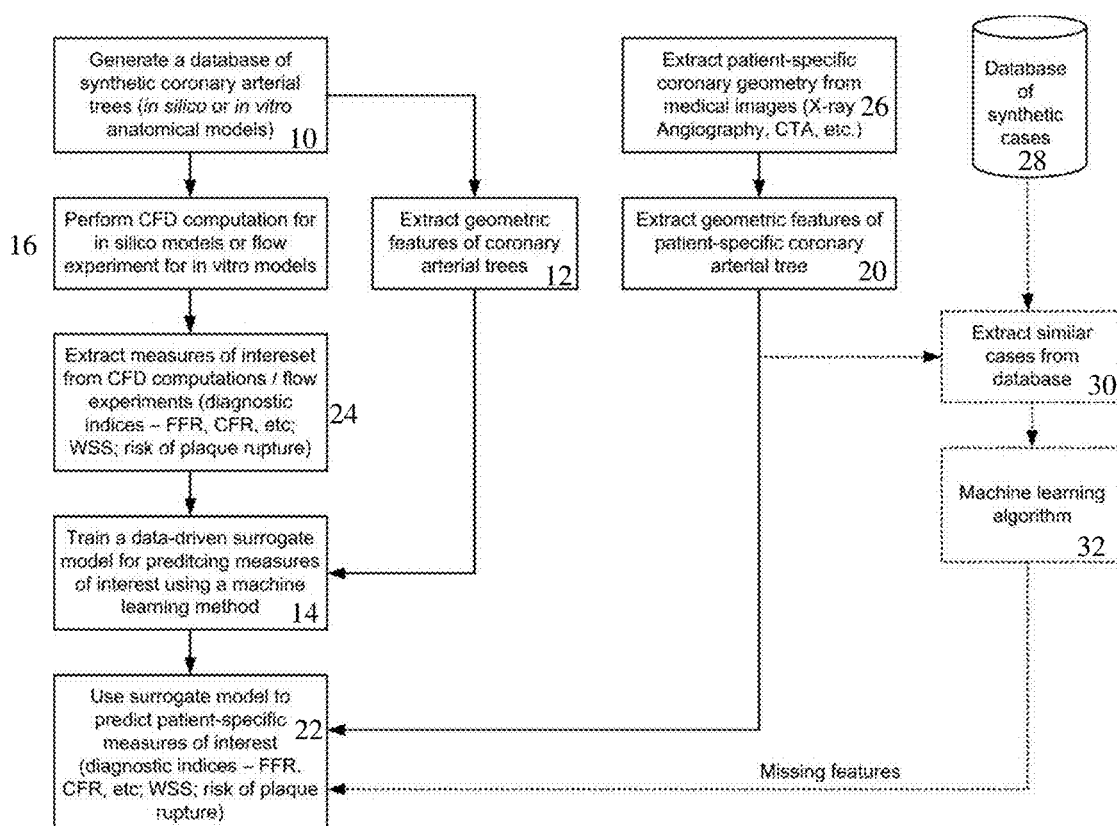
FIG. 2 is a flow chart diagram of another embodiment of a method for hemodynamic determination in medical imaging.

FIG. 2 shows another workflow or method for computing patient-specific coronary measures. Patient-specific medical imaging information is used to determine a hemodynamic metric or metrics. To predict one or more hemodynamic indices, a surrogate model is trained in act 14 using a machine learning approach. For training, a database 28 of just synthetic arterial trees is generated as training data in act 10. The database 28 is a general database. Alternatively, the database 28 is specific to an institution, such as having been created under the control of the institution. The synthetic examples are generated in silico or in vitro. In act 16, computational fluid dynamics (CFD) computations for the in silico anatomical models or flow experiments for the in vitro anatomical models are performed to determine a ground truth or value of the hemodynamic metric for each example. Depending on the metric or metrics of interest, one or more measures of interest are extracted in act 24. For instance, for coronary hemodynamics these indices may be fractional flow reserve (FFR), coronary flow reserve (CFR), instantaneous wave free ratio (iFR), and/or related quantities.

In parallel, geometric and/or other features are extracted from the synthetic examples, such as from anatomical models, in act 12. In act 14, a data-driven surrogate model(s) is trained using the geometric features and the target measure(s).

Once the surrogate model has been trained, the measures of interest may be predicted in act 22 for patient-specific geometries obtained from medical images (X-ray angiography, computed tomography angiography, magnetic resonance, or other scan) and/or other data. The patient-specific vessel geometry is extracted in act 26. Either the same features as for the synthetic data or a subset of the features are extracted in act 20 from the vessel geometry. These features are used as input data for the surrogate model.

If the patient-specific data does not include one or more features, the missing features may be either predicted from a separate machine-learnt model in act 32 or estimated using similar anatomies in the database 28 of synthetic geometries in act 30.

For training and for prediction (i.e., application of the machine-learnt classifier), features are extracted. The same set of features are extracted from the medical scan data and/or other patient specific data for application of the classifier as are used for training the classifier. The machine training may determine more discriminative features, so may provide a classifier that uses fewer of the features for prediction. For the discussion below on feature extraction, the same or different process is used to extract features from the synthetic data for training and for the patient-specific data for prediction.

In acts 10 and 26, coronary arterial trees or other vessel structures are extracted from data. For the generating from synthetic data, the extraction may be in the form of altering an existing model, creating a model that is not directly extracted from a medical scan. For generating from patient-specific data, the extraction is from medical scan data representing the vessel in two or three dimensions.

In act 10, to train a surrogate model using the machine learning approach, only synthetically generated geometries (vessel trees) are used. The synthetic geometry used during the training phase is either a full vessel tree or some part of the full vessel tree. In other embodiments, the geometry is of a single segment or branch of the vessel tree.

A starting model may be created from a given patient, but the majority of training examples are based on alterations from the starting model. Alternatively, the starting model or models are averages or other models not directly related to a given patient. The data is synthetic by not being extracted from data for particular patients. The synthetic vessel tree may have either a physical (in vitro) or a digital (in silico) representation. The digital representation is generated and stored on a computer. In alternative embodiments, some or a majority of the training examples are extracted from patient-specific data for a plurality of patients and only some of the examples are alterations of those models. If real patient anatomies are available, further synthetic trees may be constructed by stochastically perturbing the features of the patient anatomy. This added synthetic data may be used to get a richer representation, which can account for uncertainties in the data.

The in vitro synthetic models are three dimensional vessel trees artificially modeled with tubes or other devices. The in silico models are either full-scale (three dimensional) or reduced-scale models (two, one or zero-dimensional models). The number and nature of parameters and the configuration of a synthetic in silico geometry may depend on the model fidelity or scale. The highest level of detail is used for full scale models. The geometry is represented by a three-dimensional mesh, a mask, a cloud of three-dimensional points representing the arterial walls, or any other representation which describes the lumen of the vessel tree. A centerline tree may be used as input data for generating the three-dimensional mesh or the point cloud. For a two-dimensional representation, the lumen boundaries are represented by lines instead of surfaces or by a cloud of points. In a one-dimensional representation, the centerline and the effective radius at each centerline point are provided. The centerline may be represented in a one-, two-, or three-dimensional space. For a zero-dimensional in silico model, the vessel tree is represented by one or several lumped segments, whereas each segment is described by a series of parameters (e.g. resistance, compliance, or inertance) along with further parameters describing the interactions between different segments. The reduced-scale models may be determined from full-scale models by extracting the relevant information or may be generated directly.

To populate the database 28 in act 10, different approaches may be used. One or more baseline models, whose properties are then randomly or systematically perturbed to obtain a large number of models, are created. The baseline models may be represented by healthy population average coronary geometries, atlas models, and/or animal data. Other baseline models may be used.

In another approach, each model is generated separately by following a set of rules and by randomly or systematically perturbing the parameter values of these rules. Scaling laws may be used for generating realistic synthetic models.

Figure 3:
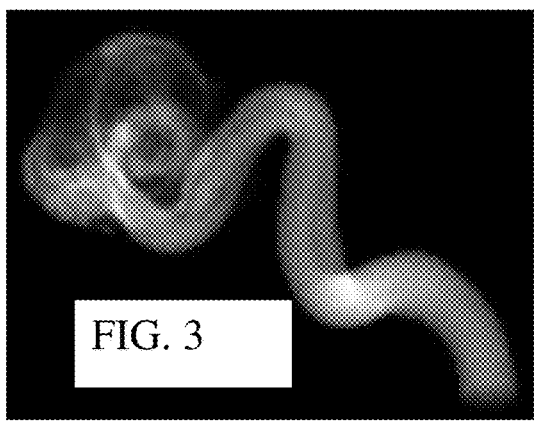
FIG. 3 is an example virtual angiogram.

The generation of synthetic data may include generating synthetic images, such as represented in FIG. 3. The synthetic image is artificially created to be similar to those obtained from different imaging modalities (angiography, computed tomography (CT), ultrasound (e.g., Echo), or other). The synthetic geometries are then extracted in act 10 from these synthetic images using the same techniques as in the case of real patient images.

FIG. 3 shows an example virtual angiogram generated to mimic an interventional exam. The virtual angiogram may then be further used to extract features related to contrast agent propagation for the synthetic geometries. For example, time density curves, transit time, blood velocity, blood flow rate, and/or other features may be determined in act 12 directly from the artificial image or from vessel geometry extracted from the artificial image.

Figure 4:
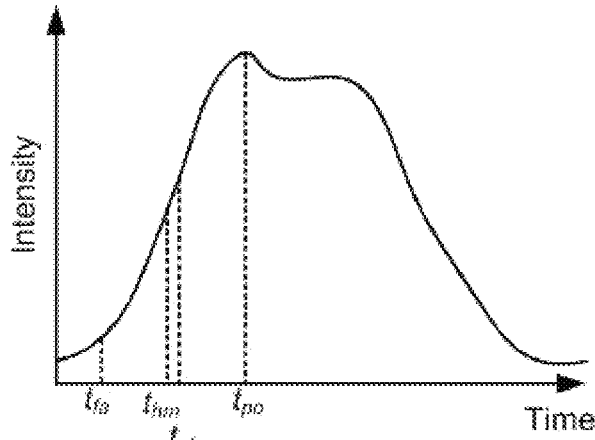
FIG. 4 is an example intensity as a function of time curve.

FIG. 4 shows a time density curve extracted from a virtual angiogram. The time density curve includes various features: $t_{ta}$ (time of first appearance), $t_{hm}$ (time to half of the peak opacification), $t_{pk}$ (time of peak gradient), and $t_{po}$ (time to peak opacification). Additional, different, or fewer features may be used.

In another embodiment, synthetic feature vectors are extracted directly in act 12 instead of first generating synthetic geometries, from which the feature vectors are then extracted. An algorithm generates the hemodynamic metrics of interest in act 24 without act 16 as well as generates the feature vector in act 12. This algorithm may use the database 28 in which synthetic geometries are mapped with synthetic feature vectors and learn how to generate directly synthetic vectors.

The large number of variations available is one benefit of using synthetic data for training. Additional examples for training are created by altering one or more values of variables for the geometric structure and/or for generating the geometric structure. Any number of different parameters may be varied. Hundreds or thousands of different examples for training may be generated from a single starting model.

Figure 5:
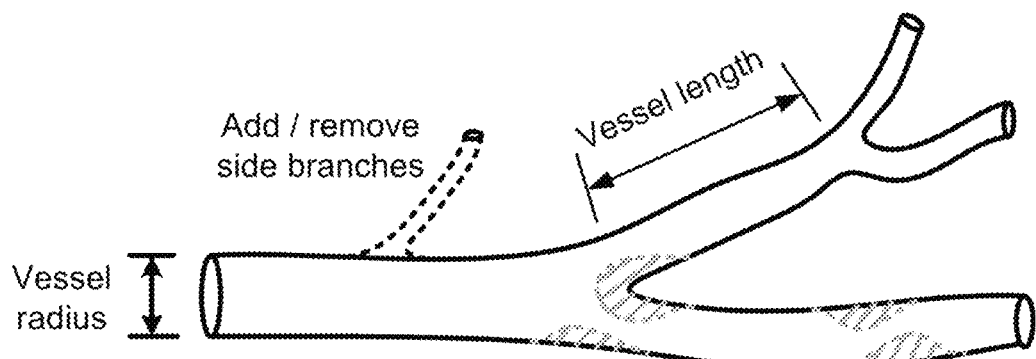
FIG. 5 illustrates a synthetic vessel model.

FIG. 5 shows an example vessel tree model and corresponding parameters that may be varied. Any number of degrees of freedom, step size in variance, or variance patterns for a given variable or combinations of variables may be used.

One parameter is the radius. The radius may be varied independently at each location or systematically along a vessel segment. Limitations on the variance may be provided, such as imposing a certain degree of vessel tapering. A reference radius value may be defined for each vessel segment. The reference radius is used as baseline for determining the radius at each location along the segment. Different rates of tapering may be used. Other geometric features which characterize local vessel size, such as the area, or effective (hydraulic) radius can also be used. The length of each vessel segment where a vessel segment is delimited by bifurcations may be varied. The vessel curvature may be varied.

Bifurcation parameters may be varied. The relationship between the radii values of the vessel segments connected at a bifurcation is varied. For example, a power law may be used at the bifurcations to describe the radiuses of the two daughter vessels:

$$r_p^\xi = r_{d1}^\xi + r_{d2}^\xi,$$

where the subscripts p, d1 and d2 refer to the parent vessel, and the two daughter vessels, respectively. The bifurcation may have more than two daughter vessels, in which case the model may be adapted as required. Different values for laminar flow, $\xi$, varying between 2.0 and 3.0 may be used.

Figure 6:
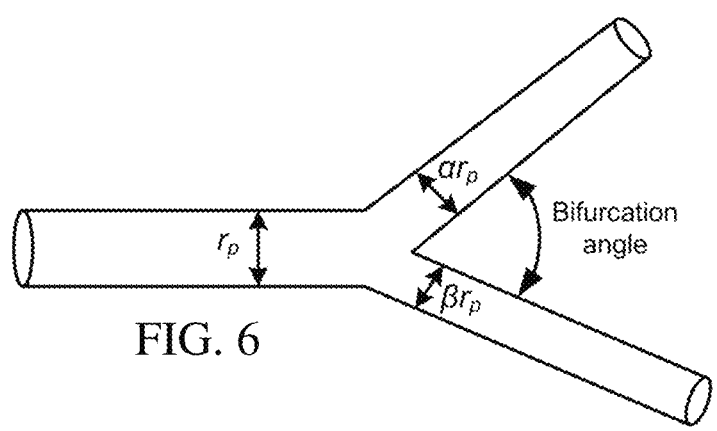
FIG. 6 illustrates bifurcation asymmetry and bifurcation angle.

Generally, the bifurcations are considered to be asymmetric, and hence the radii of the daughter vessels may be determined based on the radius of the parent vessel by using two parameters represented in FIG. 6:

$$r_{d1} = \alpha r_p, r_{d2} = \beta r_p,$$

where $\alpha$ and $\beta$ are two scaling parameters for bifurcation asymmetry. Two additional parameters are introduced, namely the area ratio and the asymmetry ratio respectively, defined as:

$$\eta = \frac{r_{d1}^2 + r_{d2}^2}{r_p^2}, \gamma = \left(\frac{r_{d2}}{r_{d1}}\right)^2.$$

The parameters $\xi$, $\eta$ and $\gamma$ are interconnected through the relationship:

$$\eta = \frac{1+\gamma}{(1+\gamma^{\xi/2})^{2/\xi}}.$$

Thus the two scaling parameters can be computed as:

$$\alpha = (1+\gamma^{\xi/2})^{-1/\xi}, \beta = \alpha\sqrt{\lambda}.$$

Other parameters and/or parameters of the geometry may be varied.

FIG. 6 shows another bifurcation parameter that may be varied to create additional examples for the database 28. The bifurcation angle is varied.

The presence, number and location, or the absence of side branches that draw the blood away from the main branches is varied. The side branches may have a major impact on the hemodynamic metric of interest, since the blood flow distribution in the entire geometry is modified. Vessel wall properties may be varied. For instance, the wall may be modeled as rigid, elastic, viscoelastic or other formulations. Depending on the model used for representing the vessel wall, different properties might be set, like wall thickness or Young's modulus. The presence and/or absence of pathologic segments (e.g. stenoses, aneurysms, coarctations, or nature of plaque) may be varied.

The location of pathologic segments may be varied. The properties of pathologic segments may be varied. These properties depend on the specific pathology considered for each geometry. For example, if atherosclerosis is considered for a synthetic model, several stenoses may be placed along the vessel tree. Different types of stenoses may be generated: single segment/bifurcation stenoses, focal, long, diffuse, or other.

Figure 7:
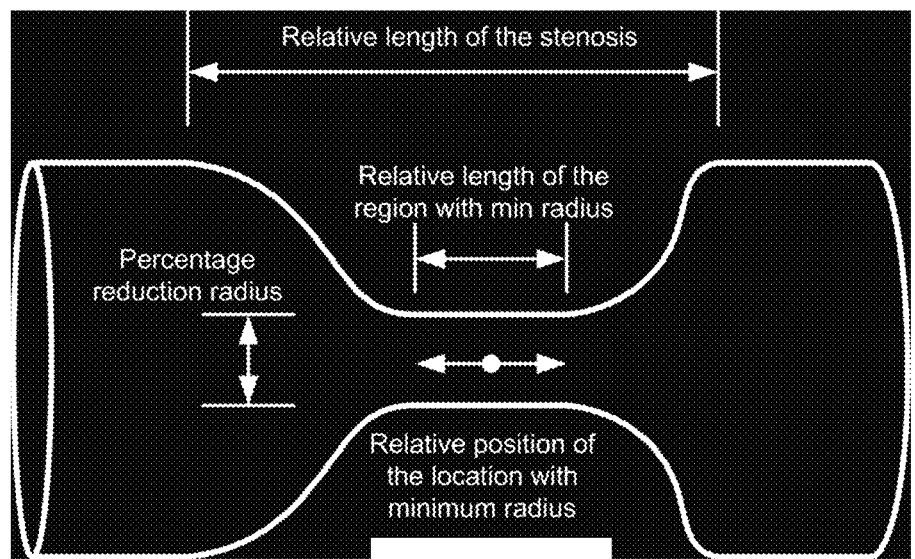
FIG. 7 illustrates a synthetic model of a stenosis.

To generate these various types of stenoses, various stenosis properties may be used. FIG. 7 shows one example set of stenosis parameters to be varied, but other parameter sets may be used. The percentage reduction of the radius at the location with minimum radius, total length, entry length, exit length, percentage diameter stenosis, tapering between start and end of stenosis, relative length of the region with minimum stenosis radius compared to the stenosis length, relative position of the location with minimum radius compared to the location of the center of the entire stenosis, inlet angle, outlet angle, eccentricity, curvature, presence and extent of calcification or plaque, and/or morphology of the plaque—for instance, lipid, fibrous, calcified or necrotic, may be varied.

Figure 8:
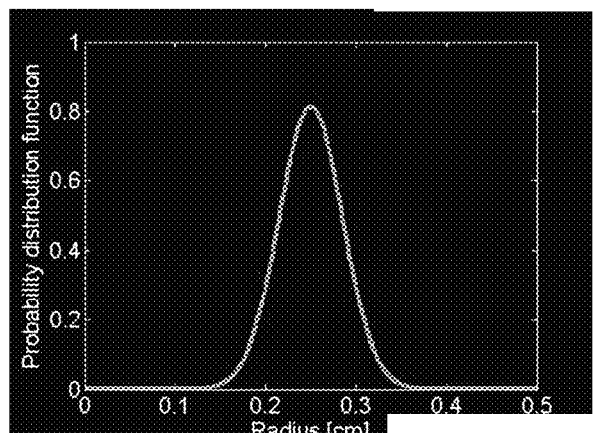
FIG. 8 shows an example normal distribution of radius of an arterial segment.

The parameters described above and/or other parameters may be modified to produce more pathological cases in the database 28. The values of the parameters are either chosen randomly for each synthetic example (e.g., true or false for binary variables or a value in a predefined range for continuous variables) or the entire parameter space is explored systematically within limited ranges when generating the database of synthetic examples. Any type of distribution may be used for the continuous variables, such as uniform, normal, or other. FIG. 8 shows an example of the normal distribution of the root radius of a coronary left arterial tree. Known, estimated, or standard normal distributions may be used. The synthetic examples generated are assigned the value for the root radius of the coronary left arterial tree based on the distribution (e.g., probability of a given value per example assigned using the distribution).

Other sources of variability may be used to create the synthetic examples for training. Parameters characterizing the coronary morphology are varied. Such parameters include type, characteristic, and/or presence or not of calcification, plaque (e.g., fibrous tissue, lipid tissue, necrotic tissue, calcified tissue), thrombus existence, diffuse disease characteristic, total or sub-total occlusion, myocardial bridging (superficial and/or deep), congenital anomalies of coronary arteries such as anomalous origin of a coronary artery from an abnormal sinus of Valsalva with an inter-arterial course between the great arteries; anomalous origin of one coronary artery from the pulmonary trunk, or others, aneurysmal dilatation and superimposed atherosclerosis, "high take off" coronary artery (i.e., the ostium is several millimeters above the sino-tubular junction (the artery may have a sharp downward angle and runs partially through the aortic wall)), myocardial bridging as either superficial or deep, coronary fistula, coronary artery dissection, coronary vasculitis as rheumatoid arthritis, systemic lupus erythematosus (SLE) or Behçet's disease, Kawasaki disease, polyarteritis nodosa, or persisting (post) inflammatory aneurysms, fibromuscular dysplasia, coronary microembolisation, and/or left or right dominance. Additional, different, or fewer morphology parameters may be used.

Figure 9:
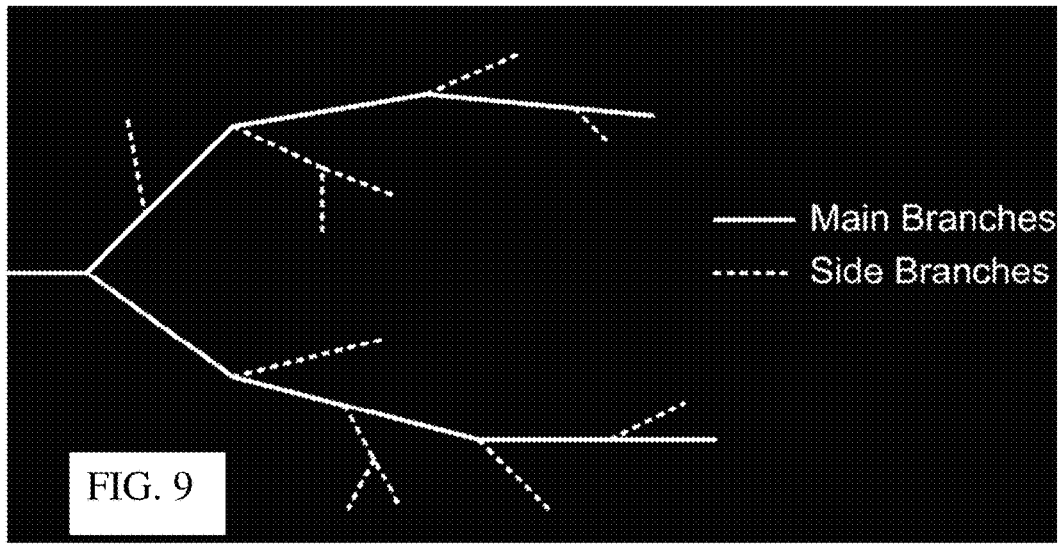
FIG. 9 illustrates an example vessel tree.
Figure 10:
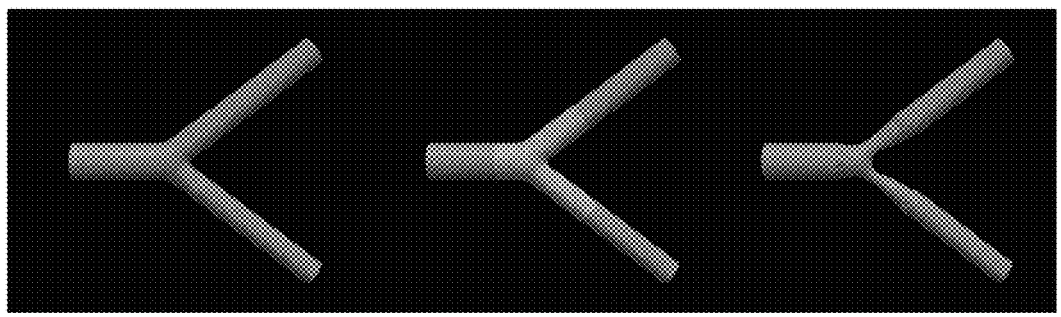
FIG. 10 illustrates an example progression of synthetic creation of a bifurcation stenosis.

FIG. 9 shows one training example of a synthetic vessel generated from an atlas. The atlas model is represented as a list of vessel segments, whereas each segment is linked to its parent and daughter segments, and the type of each segment is set to either main or side branch segment. The synthetic geometries may be generated algorithmically from the atlas in different ways. As one example, an algorithm recursively generates a one dimensional representation of the synthetic model. First, if the current segment is the root segment of the synthetic model, the start radius of the segment is computed. Next, if the segment is a side branch segment, a random binary variable is used to determine if the current segment should be used in the current synthetic model or not. Next, the length and the tapering level of the vessel segment are set using a chosen distribution function, and based on these values the bottom radius of the segment is computed. The centerline and the radius at each location along the centerline are then determined. Afterwards, another random binary variable is used to determine if a stenosis should be generated or not for this vessel segment. If a stenosis is placed on the current segment, the properties of the stenosis are set randomly from the available parameters. Finally, if the current segment has daughter segments, the function is called for each daughter segment so as to traverse the entire atlas model. A sample algorithm for this approach of generating synthetic geometries is presented below

```
generateRandomSyntheticGeometry(currentSegment)
        if(currentSegment is root segment)
                currentSegment → topRadius = getRandomValue (r_min, r_max)
        end_if
        if(currentSegment is side branch segment)
                if(currentSegment → getRandomBinary)
                        currentSegment →excludeFromGeometry( )
                        return;
                end_if
        end_if
        currentSegment → length = getRandomValue (length_min, length_max)
        currentSegment → tapering = getRandomValue (taper_min, taper_max)
        currentSegment → bottomRadius = computeBottomRadius(currentSegment
→ topRadius, currentSegment → tapering, currentSegment → length)
        currentSegment → computeCenterlineAndRadiusAtEachLocation( )
        if(currentSegment → getRandomBinary( ) )
                currentSegment → generateStenosis( );
        end_if
        if(currentSegment has daughter segments)
                if(currentSegment → getRandomBinary( ) )
                        currentSegment → generateBifurcationStenosis( );
                end_if
                currentSegment → computeRadiusOfDaughterSegments( )
        end_if
        for(each daughter segment of currentSegment)
                generateRandomSyntheticGeometry(currentSegment →
daughterSegment[i])
        end_for
```

Other programs using different or additional sequences, parameters, or process acts may be provided.

Once a synthetic geometry is generated, it may be further modified, such as adapting the stenosis properties. FIG. 1 represents an example approach for creating synthetic bifurcation stenosis, where the limits for the stenosis are decided either automatically or manually. A model is used to deform the geometry. Once the bifurcation location is identified as assigned a stenosis, the stenosis parameters are assigned, resulting in a given level and/or type of stenosis.

Other examples are generated by processing the same atlas again and/or by processing the resulting example as if an atlas. Other synthetic examples may be created using other approaches, such as starting with a three-dimensional model. Rather than varying in steps, the parameters to be varied may be randomly selected and then random values assigned.

Using synthetic modeling instead of requiring examples from a large collection of patients for training data provides several advantages. A very large number of cases may be automatically generated, leading to an extensive database. Complex pathological configurations may be generated, such as serial stenoses, multi-branch stenoses, bifurcation stenoses, diffuse disease, or others, despite being rare among actual patients. Rare pathological cases may be sampled better. Since the generation of synthetic in silico geometries may be completely automated, the cost of generating a large database is reduced as compared to assembling patient examples. The examples may be extended to different demographic groups easily. The training may be done in a global manner or a site-specific manner, allowing the system to account for anatomical trends based on patient demographics and epidemiology. Finding sufficient examples in a local region may be difficult. The training may be iteratively improved with either more data or with better representations of the features.

Once the synthetic geometries have been generated, the features which are used for training the machine learning algorithm are extracted in act 12. The same features or some subset of the features are extracted from the medical images of the patient in act 20 and used for predicting the hemodynamic metric using the trained model. Depending on the source and type of the input data, the extracted features may be binary, numerical, categorical, ordinal, binomial, interval, text-based, or combinations thereof.

The extraction includes assigning features or calculating features. For example, a geometrical feature randomly generated for creating the synthetic vessel tree is used as an extracted feature by assignment. As another example, a difference between two features is calculated from the created vessel tree.

Any type of features may be used. Morphological features may be used. The machine learning process may provide for certain features to be used and others not to be used. To train, the features to be used may be selected by a programmer.

Some example features include the parameters used or selected to define or create the vessel structure as described above. Other or different features may additionally or alternatively be extracted.

Figure 11:
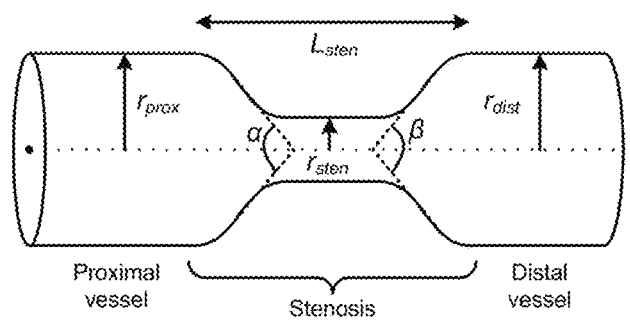
FIG. 11 shows example geometrical features describing a shape of a stenosis.

Geometric features of the vessel structure are extracted. Geometric features characterizing the geometry of a stenosis may be extracted. Parameters characterizing the geometry of the stenosis include reference diameters (e.g., proximal and distal), minimal lumen diameter (MLD), lesion length (LL), minimum radius length (e.g., length of the stenosis in the region of minimum radius—a tolerance limit can be used for detecting this region around the location with minimum radius), entrance angle, entrance length, exit angle, exit length, % diameter of stenosis (e.g., computed based on proximal and/or distal reference radii), or % area stenosis (e.g., computed based on proximal and/or distal reference areas). FIG. 11 shows an example set of stenosis features. Additional, different, or fewer features may be extracted. Various combinations obtained through algebraic, integration, or derivation operations applied for proximal, distal and minimum radius of the stenosis, or any other stenosis-specific, may be additionally used.

Features may be extracted for the geometry of the branch bearing the lesion. Features characterizing the branch geometry include vessel radius sampled along the centerline, areas sampled along the centerline, terminal radius of the vessel tree, terminal area of the vessel tree centerline tortuosity measures, location of stenosis in coronary tree, cumulative or aggregated number of vessel narrowing proximal to the lesion, cumulative number of calcifications proximal to the lesion, and/or vessel type (e.g., left anterior decent (LAD), left circumflex (LCx), right coronary artery (RCA), diagond (D), optimum modulus (OM), and/or others). Additional, different, or fewer parameters may be used.

One or more coronary tortuosity measures may be used. Given a discrete curve as a set of points in three dimensions, a spline interpolation is first performed to determine a continuous curve C(x(t), y(t), z(t)), with t taking values between $t_0$ and $t_1$. Next, the following measures are computed:

Arc length: $arcLength(C) = \int_{t_0}^{t_1} \sqrt{x'(t)^2 + y'(t)^2 + z'(t)^2} \, dt$;

Chord length: $chordLength(C) =$
$$\sqrt{(x(t_1) - x(t_2))^2 + y(t_1) - y(t_2))^2 + z(t_1) - z(t_2))^2}$$ ;

Curvature: $\kappa(t) = \frac{\|r'(t) \times r''(t)\|}{\|r'(t)\|^3}$, where $r'(t) = (x'(t), y'(t), z'(t))$ and $r''(t) = (x''(t), y''(t), z''(t))$;

Total curvature: $t_{sc} = \int_0^{arcLength} \kappa(s) ds$ where s is the arc length variable along the curve; and Total squared curvature: $t_c = \int_0^{arcLength} \kappa^2(s) ds$ Based on these measures, many tortuosity measures may be defined, some of which are given as:

$\tau_0 = \frac{chordLength}{arcLength}$, $\tau_1 = \frac{arcLength}{chordLength} - 1$, $\tau_2 = t_c$, $\tau_3 = t_{sc}$, $\tau_4 = \frac{t_c}{arcLength}$, $\tau_5 = \frac{t_{sc}}{arcLength}$, $\tau_6 = \frac{t_c}{chordLength}$, and/or $\tau_7 = \frac{t_{sc}}{chordLength}$.

Additional, different, or fewer measures may be used.

Features characterizing the entire coronary tree may be extracted. The features for the coronary tree may include: left or right dominance, size of coronary territories and associated myocardial masses, terminal radius of each coronary branch, number of lesions, segments with lesions, bifurcations with any number of daughter vessels (e.g., type and angulations), number and location of stents already implanted, and/or number and location of bypass grafts. Additional, different, or fewer features for the entire coronary tree may be used.

Other geometric features may be extracted. For geometric or other features, a set of naming conventions defining aspects of the vessel structure are described. A centerline tree is constructed for a given coronary arterial tree. The infinite number of points in the centerline tree may be classified into a start point (i.e., the first point of the centerline tree, corresponding to the ostium), zero, one or more ramification points (i.e., a point where the centerline bifurcates into two or more centerline segments), an end point (i.e., a point for which no further downstream centerline point exists), and interior points (i.e., points lying between a start/ramification point and a ramification/end point). Each coronary segments are classified as a root segment (i.e., a segment delimited by a start and a ramification point), a branch segment (i.e., a segment delimited by two ramification points), or a leaf segment (i.e., a segment delimited by a ramification and an end point). Each coronary segment (e.g., root, branch, or leaf) is labeled as either a non-healthy segment (i.e., a segment that has an abnormal luminal narrowing or dilation) or a healthy segment (i.e., a segment that has no abnormal luminal narrowing or dilation). Other naming conventions, classifications, or labeling may be used.

Other features extracted include parameters for one or more abnormalities of the vessel structure. Abnormal morphology may be characterized by characteristics of calcification, characteristics of the plaque (e.g., fibrous tissue, lipid tissue, necrotic tissue, calcified tissue), characteristics of thrombus, characteristics of diffuse disease, presence of total or sub-total occlusion, presence of myocardial bridging (superficial and/or deep), congenital anomalies of coronary arteries (e.g., anomalous origin of a coronary artery from an abnormal sinus of Valsalva with an inter-arterial course between the great arteries, anomalous origin of one coronary artery from the pulmonary trunk, or others), aneurysmal dilatation and superimposed atherosclerosis, "high take off" coronary artery (e.g., the ostium is several millimeters above the sino-tubular junction (the artery may have a sharp downward angle and runs partially through the aortic wall)), myocardial bridging: superficial and deep, coronary fistula, coronary artery dissection, coronary vasculitis (e.g., rheumatoid arthritis, systemic lupus erythematosus (SLE), or Behçet's disease, Kawasaki disease, polyarteritis nodosa, and/or persisting (post) inflammatory aneurysms), fibromuscular dysplasia, coronary micro embolization, and/or left or right dominance. Additional, different, or fewer abnormality features may be used.

Functional features representing operation of the vessel structure may be extracted. Functional information includes functional imaging, such as measures of uptake, or other operational information, such as contrast agent measures. For the training data, the functional features may be determined from simulation, synthetically created images, modeling, and/or other representation of the operation of the vessel.

In addition to anatomic and morphological features from medical images or synthetic representation of a vessel tree, functional features may also be extracted. For example, data from a perfusion scan or other medical imaging scan (e.g., single photon emission computed tomography (SPECT), positron emission tomography (PET), or perfusion imaging) may also be used to extract features such as metrics characterizing relative and/or absolute tissue perfusion in each coronary territory at rest and/or during stress. As another example, angiographic data may characterize contrast agent propagation. Some features characterize the flow of contrast at a given location, such as the time-to-peak tracer concentration, and splits across different daughter vessels at a bifurcation.

Figure 12:
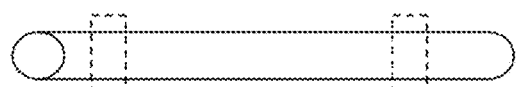
FIG. 12 shows example region of interest identification on a vessel.
Figure 13:
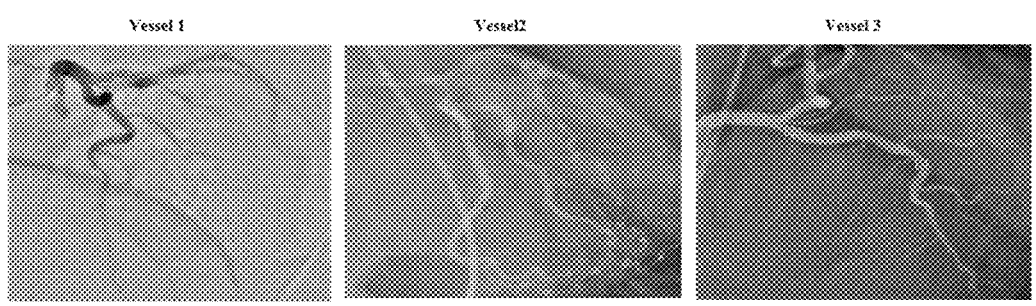
FIG. 13 shows example placement of distal and proximal regions of interest on vessels visualized in angiography.

Some characteristics are extracted based on two regions of interest (ROI) defined for vessel trees. FIG. 12 shows two ROIs for a synthetic representation of a vessel segment. Since direct measures of function (e.g., perfusion or transit time) are not available for in silico synthetic data, modeling may be used. For in vitro synthetic data, direct measures, such as medical scan or measuring optically, may be used. Alternatively, one or more synthetic images are generated to represent function. FIG. 13 shows distal and proximal ROIs on three vessels from synthetic or actual patient angiography scans.

One metric to be extracted is the transit time or the time required for the contrast agent to traverse the distance between the two ROIs. The transit time may be estimated using manual, semi-automated, or fully-automated methods. Manual methods include counting the number of frames required for the contrast agent to traverse the distance between the ROIs. Combined with the frame rate of the sequence, the transit time is estimated. Semi-automated methods include manual placement of the ROIs on each frame. Since the coronary vessels are continuously moving, the actual locations of the ROIs change from one frame to another. The transit time is automatically estimated from the manually placed ROIs and the data. The automated estimation of transit time is based on time density curves (TDCs). A TDC across a vessel's region of interest is the surface integral of the pixels' intensities inside the ROI:

$$D(t) = \iint I(x,y,t) dx dy$$

where l(x,y,t) represents the pixels' intensities at the acquisition time t and D(t) is the time density curve.

Figure 14:
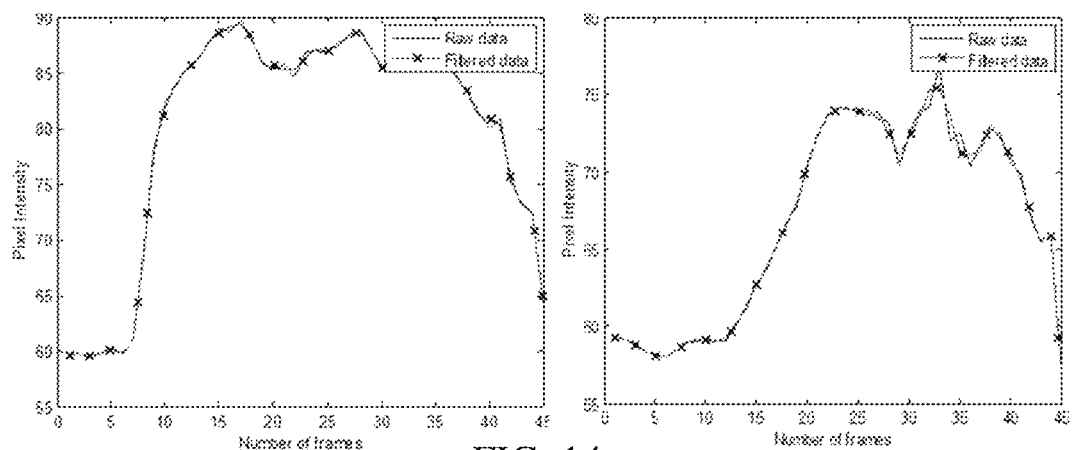
FIG. 14 shows example graphs of Savitzky-Golay filtering for proximal and distal regions of interest.

Several noise sources may distort the shape of the time density curve and thus introduce errors in the estimation of transit time. The sources of noise include recirculation of the contrast material, extravascular accumulation of contrast material that produces a lower peak and a slower washout, shape of the contrast bolus (especially for manual injection), non-steady flows that may be observed when the contrast agent does not fully mix with the blood, and/or opacification of background structures (bones). Before applying different methods for transit time estimations, the computed time density curves are post-processed through normalization, filtering and curve fitting. As an example, a filtering with a Gaussian weighted moving average or a Savitzky-Golay filtering is used. FIG. 13 shows angiographic images after Savitzky-Golay filtering. Other filtering may be used. FIG. 14 shows Savitzky-Golay filtering for proximal ROI (left) and distal ROI (right) ROIs. Alternatively, a fitting of the time density curve may be performed, identifying thus for example a complex exponential function (Gaussian or gamma variate function—Error! Reference source not found.) or a polynomial function that preserves the key characteristics of the slope (e.g., peak value, the delays of contrast appearance, and/or the washout slope).

Figure 15:
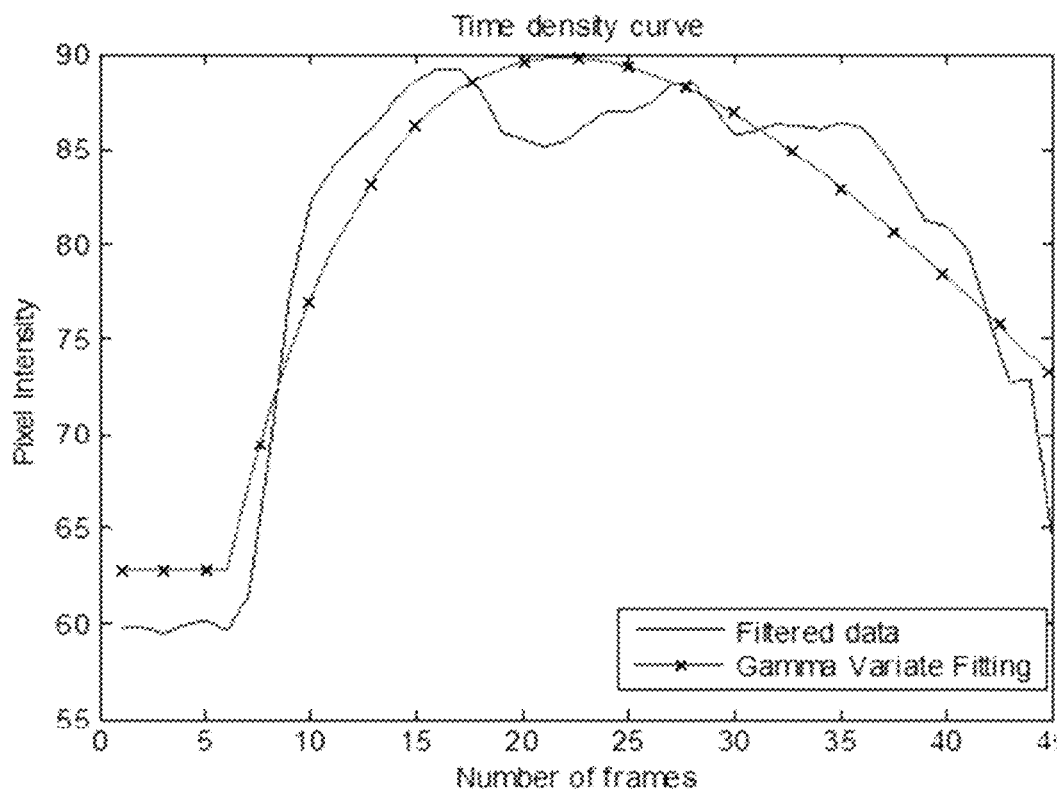
FIG. 15 illustrates an example of gamma variate filtering of a time density curve.

In one embodiment, the transit time is determined by selecting two ROIs along a same vessel. The time density curves for the two ROIs are extracted. The time density curves are smoothed, such as with Savitzky-Golay or other filtering. A curve is fit to the time density curves. Any curve fitting may be used, such as fitting of a gamma variate function as represented in FIG. 15. The transit time is estimated based on the two time density curves (raw, smoothed and/or fitted). Various transit times may be used, such as:

$$\text{mean transit time: } t_{mtt} = \frac{\int_0^\infty t \cdot D(t) dt}{\int_0^\infty D(t) dt};$$

mean transit time after curve thresholding:

$$D(t) = \begin{cases} D(t) - \Delta & \text{if } D(t) > \Delta \text{ with } \Delta = \alpha \cdot \max_t D(t) \\ 0 & \text{otherwise} \end{cases};$$

time of peak opacification (i.e., the bolus is considered to have arrived at a ROI when the time-density curve reaches its peak value);
time to half max (i.e., the bolus is considered to have arrived once the time-density curve reaches half of its peak density);
first appearance time (i.e., the bolus is considered to have arrived when the density reaches 5% of its peak value) $D(t_{fa})=0.05 \cdot D_{max}$;
rise time: $t_{rt}=t_{max} - t_{fa}$ where the reference time is $t_{fa}$ (the first appearance time);
mean concentration time (i.e., the bolus is considered to have arrived when the density reaches the mean value for the first time);

$$\text{mean arrival time } t_{mat} = \frac{1}{D_{max}} \int_{t_{ref}}^{t_{max}} [D_{max} - D(t)] dt$$

where $t_{mat}$ is the mean arrival time, $t_{ref}$ is the reference time, and $t_{max}$ is the peak time;
time of peak gradient (i.e., the bolus is assumed to have arrived when the gradient of the time-density curve reaches its maximum value); and/or
cross correlation method (i.e., the time-density curve obtained at the first ROI is shifted in time so that the curve superimposes the curve obtained at the second ROI where the $\Delta t$ value that maximizes the cross-correlation function $\varphi(\Delta t)=\int_0^{t_{end}} D_{ROI1}(t-\Delta t) \cdot D_{ROI2}(t) dt$ is considered to be the time of bolus transport between the two ROIs. Additional, different, or fewer transit time features may be extracted.

Once the transit time is determined, other features may be estimated. As examples, the other features include: the velocity of the contrast agent (e.g., may be computed from the transit time and the distance between the two ROIs along the centerline of the vessels), and/or the flow rate of the contrast agent may be computed from the transit time and the vessel volume between the two ROIs. Additional, fewer, or different features may be used.

Yet another example of features to be extracted are an ischemic weight and/or ischemic contribution. Some features based entirely on geometry include ischemic weight w and ischemic contribution score s. An ischemic weight value is associated to each coronary segment (root, interior or leaf segment). An ischemic contribution score is computed for a specific nonzero, finite length segment of coronary geometry, comprising one or more branches. The ischemic contribution score is computed from a series of geometric properties and from the ischemic weights of the particular segments.

Figure 16:
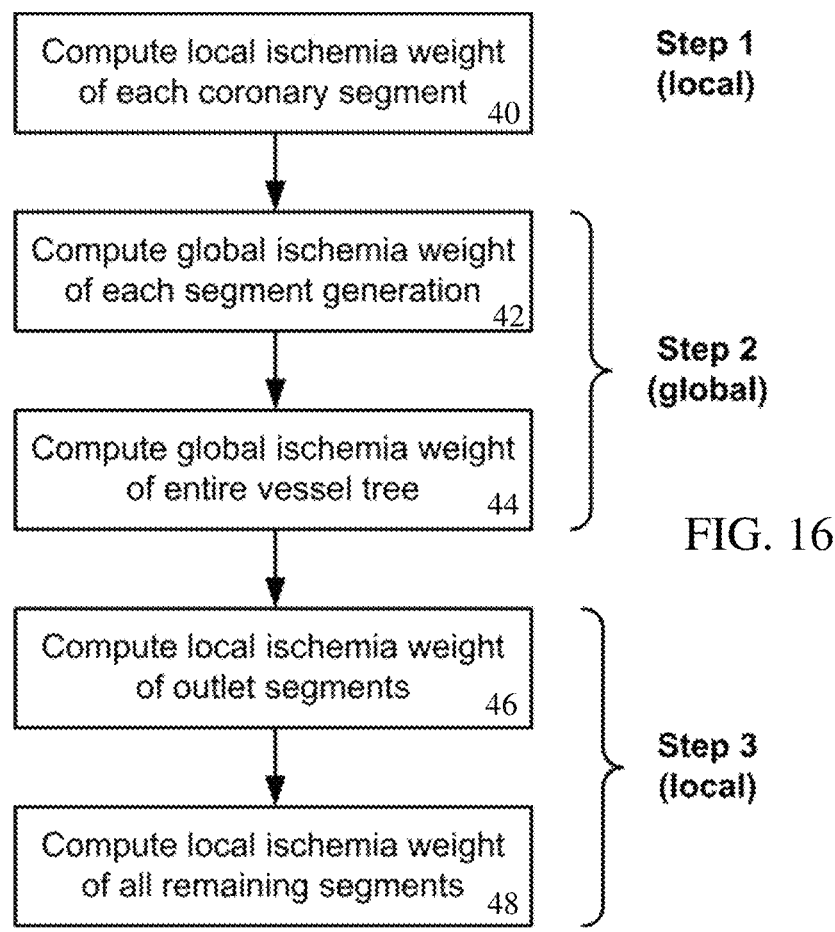
FIG. 16 is a flow chart of one embodiment of a method for calculating ischemic weight for a coronary artery segment.

For ischemic weight, the ischemic weight value, w, of each coronary segment corresponds to the sum of the ischemic weight values of all downstream segments. To compute the weights, a three step local-to-global-to-local approach shown in FIG. 16 is used. A separate ischemic weight is computed for each branch in act 40. A local ischemia weight value is estimated independently for each root/branch/leaf segment using geometric features of the segment, such as the reference radius, length, tapering rate and other features. As an example, the ischemic weight could be computed using:

$$w = k_1 \cdot r_{ref}^n,$$

where, $r_{ref}$ is the reference radius of the segment, $k_1$ is a proportionality constant, and n is a power coefficient. Since, regularly, the radius along the centerline of a segment, r(x), is continuously varying, a mathematical operator ($f_1$) is applied to compute the reference value:

$$r_{ref} = f_1(r(x)).$$

An average value of healthy radiuses of the entire branch or a part of the branch, an average value of healthy radiuses obtained when excluding the largest x % and the smallest y % of the radius values of the entire branch or a part of the branch, or maximum or minimum value of healthy radii of the entire branch or part of the branch are computed.

Figure 17:
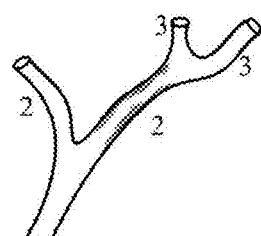
FIG. 17 shows an example coronary tree labeled by segment.

As the local weights are computed independently, there is no guarantee that the assumption that the sum of the ischemic weights of two daughter branches is equal to the ischemic weight of the parent branch holds. Therefore, one global ischemic weight for the entire tree is computed by averaging the weights of different branches in different generations. For example, a global ischemia weight value for the entire coronary tree (left or right coronary tree) based on ischemia weights $w_i$ is determined. In act 42, a global ischemia value for each generation of vessels is computed. FIG. 17 shows an example of a coronary tree where a generation number, g, is attached to each branch. The root branch has a generation number of 0, which then increases at each bifurcation by one. Before estimating the global ischemia weight, a confidence value $c_i$ is attached to each branch. The confidence value represents the confidence in the correctness of the computed reference radius or other geometric parameter. Very short branches, such as the bottom branch with generation number equal to 1 in FIG. 17 or entirely diseased branches, such as the diffusely diseased branch with generation number equal to 2 in 17 receive a low confidence value, while long vessels without radius irregularities receive large confidence values. During model development, other constraints may also be applied using known optimization methods.

In act 44, the global ischemia value for generation g is computed using a mathematical operator $f_2$:

$$(w_{global})_g = f_2(c_i, w_i)$$

where index i refers to all branches of generation g and all terminal branches with a generation number smaller than g. For example, $(w_{global})_g$ is computed from:

$$(w_{global})_g = \sum_i c_i \cdot w_i$$

Next, a final global weight value is computed from the individual global weights $(w_{global})_g$ corresponding to a single generation. Again, a confidence value may or may not be attached to each generation, $d_j$, and the final global weight value is determined using a mathematical operator $f_3$:

$$w_{global} = f_3(d_j, (w_{global})_j),$$

where index j refers to a generation number. For example, the global weight is computed as a weighted mean:

$$w_{global} = \frac{\sum_j d_j \cdot (w_{global})_j}{\sum_j d_j}.$$

Other functions may be used.

In acts 46 and 48 of FIG. 16, the global ischemic weight is distributed to the individual branches in a way that satisfies the original assumption. During the third step (local), starting from the global ischemia weight, a final local ischemia weight value is computed for each root/branch/leaf segment. In act 46, the local weight of the coronary leaf segments:

$$w_k = \frac{(r_{ref})_k^n}{\sum_k (r_{ref})_k^n} w_{global}$$

is computed, where k refers to the coronary leaf segments. Finally, the ischemia weights of the branch and root segments are computed in act 48 as a sum of the ischemia weights of all downstream leaf segments:

$$w_l = \sum_k w_k,$$

where k refers to all leaf segments lying downstream from the current segment l. Other functions may be used. Other representations of ischemic weight may be used.

Ischemic contribution score may be computed as a feature for a vessel tree. The ischemic contribution is a function of the ischemic weight and a geometric parameter, such as radius. The ischemic contribution score is computed for a nonzero finite length coronary artery segment that may or may not contain ramifications.

Figure 18:
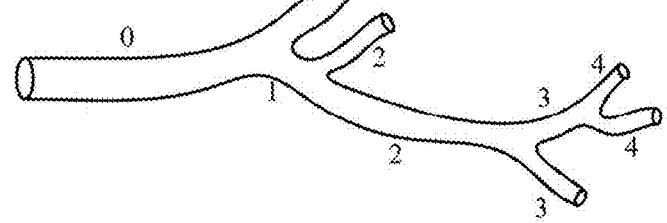
FIG. 18 shows an example coronary tree with ischemic weights and longitudinally varying cross-sectional radii in a healthy anatomical model.

The ischemic contribution score is computed differently for healthy and non-healthy segments. Healthy segments have low ischemic contribution scores. For a healthy coronary artery segment, like the one in FIG. 18, the ischemic contribution score s is computed using the formula:

$$s = k_2 \int_0^L \frac{w(x)}{r(x)^n} dx,$$

where L is the total length of the segment, $k_{21}$ is a proportionality constant, n is a power coefficient, r(x) is the radius that varies along the centerline, w(x) is the ischemic weight, which may vary along the centerline if ramifications are present. FIG. 18 shows a representation of a vessel segment with multiple bifurcations, corresponding ischemic weights, and longitudinally varying cross-sectional radiuses in a healthy anatomical model.

Non-healthy segments, such as shown in FIG. 17, have higher ischemic contribution scores. Higher the severity of the lesion result in higher ischemic scores. In this example, the segment is non-healthy due to stenosis, but a same or similar approach may be used for other types of pathologies (e.g. aneurysm). For a stenosis that stretches along a single root/branch/leaf segment, the ischemic contribution score is computed using the formula:

$$s = f_4(r(x))w_l + f_5(r(x))w_l^2,$$

where $f_4$ and $f_5$ are mathematical operators applied to the longitudinally varying radius and $w_l$ is the weight of the segment. The two components in the contribution score may be used separately as features for training the surrogate model, and/or each component may be divided into subcomponents that are then used as features. Other functions may be used.

Figure 19:
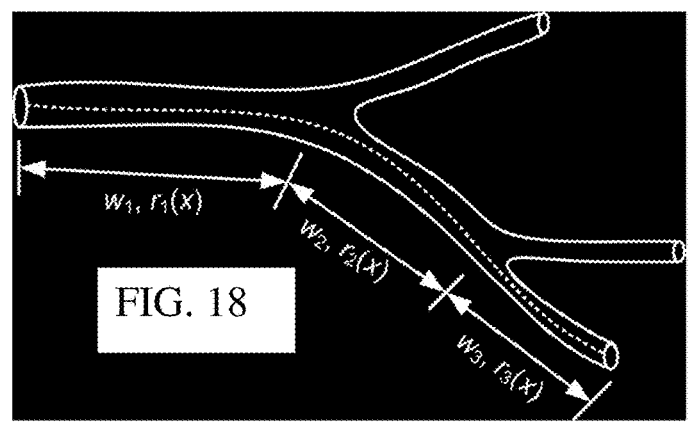
FIG. 19 shows an example partially diseased vessel segment and corresponding ischemic contribution score.
Figure 20:
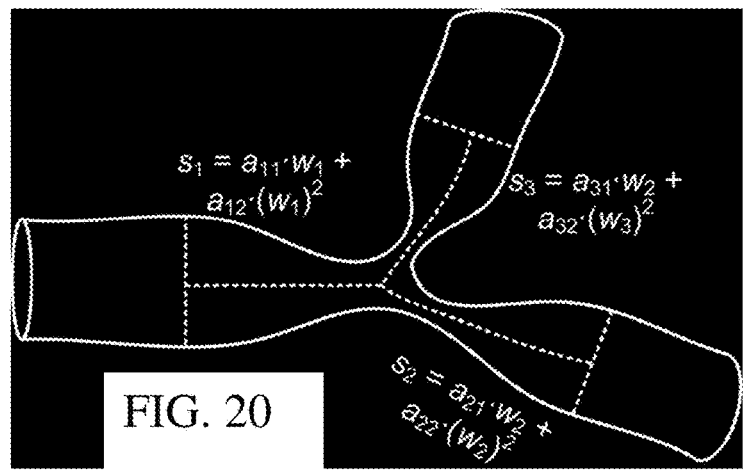
FIG. 20 shows an example computation of ischemic contribution score for a bifurcation lesion.

FIG. 19 shows one embodiment of a vessel branch or segment that includes healthy portions and a non-healthy portion, a partially diseased vessel. The ischemic scores are computed separately for these different parts. In a case of bifurcation stenosis as represented in FIG. 20, the stenosis stretches along several root/branch/leaf segments. A separate ischemic contribution score is computed for each root/branch/leaf segment of the stenosis pertaining to either the parent or the daughter branches as represented in FIG. 20. Other approaches, such as using a combined score for the bifurcation, may be used.

Other ischemic features may be computed. For example, based on the ischemic contribution scores of individual segments, features representing cumulative ischemic contribution scores may be computed at any location in a coronary arterial tree. Various features include: cumulative ischemic contribution score computed from all segments lying between the root segment and the current locations, cumulative ischemic contribution score computed from the healthy segments lying between the root segment and the current locations, cumulative ischemic contribution score computed from the pathologic segments lying between the root segment and the current locations, cumulative ischemic contribution score computed from all segments lying between the current location and a leaf segment (e.g., the path from the current location to the leaf segment may be determined by choosing at each ramification the path along the main daughter segment, as determined from a combination of properties such as reference radius, total length downstream, and total number of generations downstream), cumulative ischemic contribution score computed from the healthy segments lying between the current location and a leaf branch, and/or cumulative ischemic contribution score computed from the pathologic segments lying between the current location and a leaf branch. Additional, different, or fewer ischemic features may be computed.

The ischemic contribution scores and/or the other geometric features enlisted above may be computed separately for all pathologic segments lying upstream and downstream from the current location. Then, the features may be ordered based on a chosen criterion (e.g., ischemic contribution score or some other feature) and used as an ordered list of features.

Figure 21:
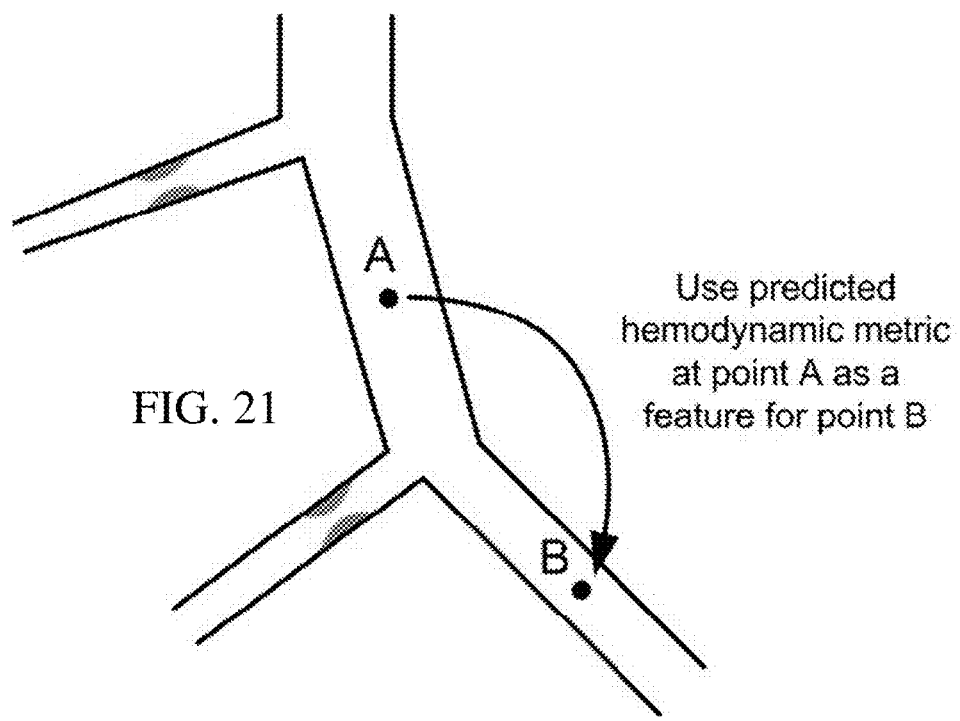
FIG. 21 illustrates an example use of predicated hemodynamic metric at upstream locations as a feature to predict the hemodynamic metric at a downstream location.

Features for describing the interaction between branches of vessels may be extracted. For example, the hemodynamic metric itself, estimated using a machine learning algorithm at an upstream location in the vessel tree may be used as a feature for the estimation of the hemodynamic metric at a downstream location and vice-versa. For example, as displayed in FIG. 21, the predicted hemodynamic metric at point A may be used as a feature to predict the hemodynamic metric at point B.

Figure 22:
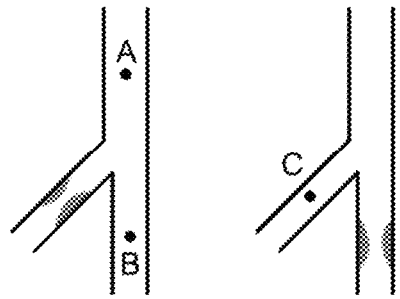
FIG. 22 illustrates an example of flow interaction between vessels.

Other features may be defined that account for interaction of flow across different, possibly not neighboring, vessel segments. For example, in FIG. 22, the hemodynamics at points A and B are influenced by the stenosis on the side branch. The presence of the stenosis leads to a decreased flow in the parent, and hence to a lower pressure in the parent branch. This in turn influences the absolute pressure in the daughter branch to which point B belongs. Similarly, the presence of the stenosis in the main branch influences the hemodynamics at point C. The stenosis leads to a lower flow and a lower pressure drop in the parent branch and, thus to different absolute pressure levels in the side branch.

Figure 23:
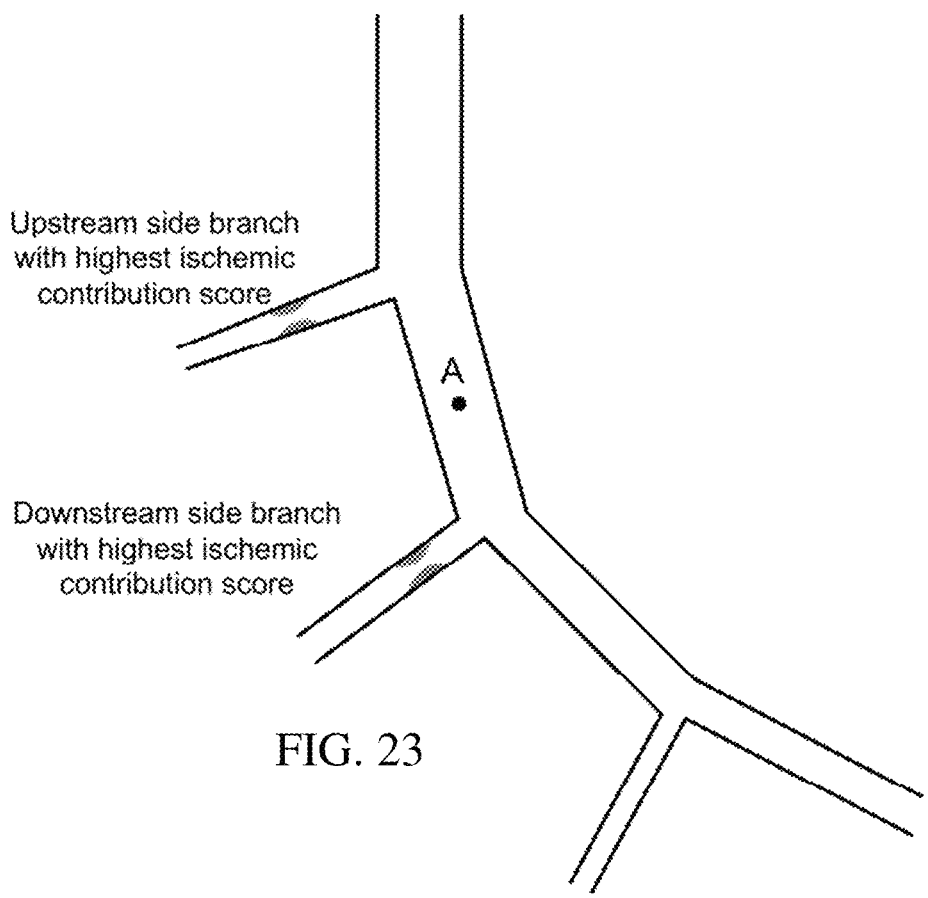
FIG. 23 shows an example vessel tree with stenosis on side branches.

Any approach may be used to account for the interaction between the vessels. A new feature may capture the interaction. Alternatively or additionally, existing features are modified to account for the iteration. For a new feature, a combination of the features described for the different side branches or segments are used for a location on a main branch. Similarly, for a location on the side branch, additional features computed for the main branches may be used. For example, when generating the feature vector for location A in FIG. 23, the total contribution score of the upstream side branch with the most severe stenosis and the total contribution score of the downstream branch with the most severe stenosis may be added as features. Any other feature or combination of features may be used for this purpose.

For modification of other features to account for interaction, the ischemic weights of the individual segments are modified in one example. This modification may in turn lead to an adaptation of all features based on ischemic contribution score. The first step is to determine a local decrease of the ischemic weight separately for each segment:

$$\Delta w_l = f_6(w_l, s_l(w_l)),$$

where $w_l$ is the ischemic weight of the current segment and $s_l$ is the ischemic weight of the current segment, and $f_6$ is a mathematical operator.

Since each segment has a different $\Delta w_l$ value, these changes are used at a global level to adapt the ischemic weights so as to make sure that the original assumptions hold (i.e., the sum of the ischemic weights of two daughter branches is equal to the ischemic weight of the parent branch).

The ischemic weights are globally adapted in a top-down or a bottom-up approach. For the top-down approach, the weights are adapted from the root of the tree. Thus, the new ischemic weight of the parent (root) branch is determined as:

$$w'_l = f_7(w_l, \Delta w_l)$$

where $w'_l$ is the new ischemic weight of the parent branch. Next, the new ischemic weights of the leaf segments downstream from the current segment are computed as:

$$w'_k = \frac{(r_{ref})_k^n}{\sum_k (r_{ref})_k^n} w'_l.$$

The ischemic weights of the branch lying between the current branch/and the leaf branches k are computed as a sum of the ischemia weights of all downstream leaf segments. Afterwards, the computations are repeated for all daughter branches of the current branch, and the process is repeated recursively until the entire tree is traversed and the leaf branches are reached.

For the bottom-up approach, the ischemic weights of the leaf branches are adapted as:

$$w'_k = f_8(w_k, \Delta w_k).$$

Next, the ischemic weight of the parent branch is adapted using:

$$w'_l = f_9(w_l, \Delta w'_l, \ldots, w'_j),$$

where l refers here to the parent branch, while $w'_l \ldots w'_j$ refer to the new ischemic weights of the immediate daughter branches. This process is repeated recursively until the root branch is reached.

Figure 24:
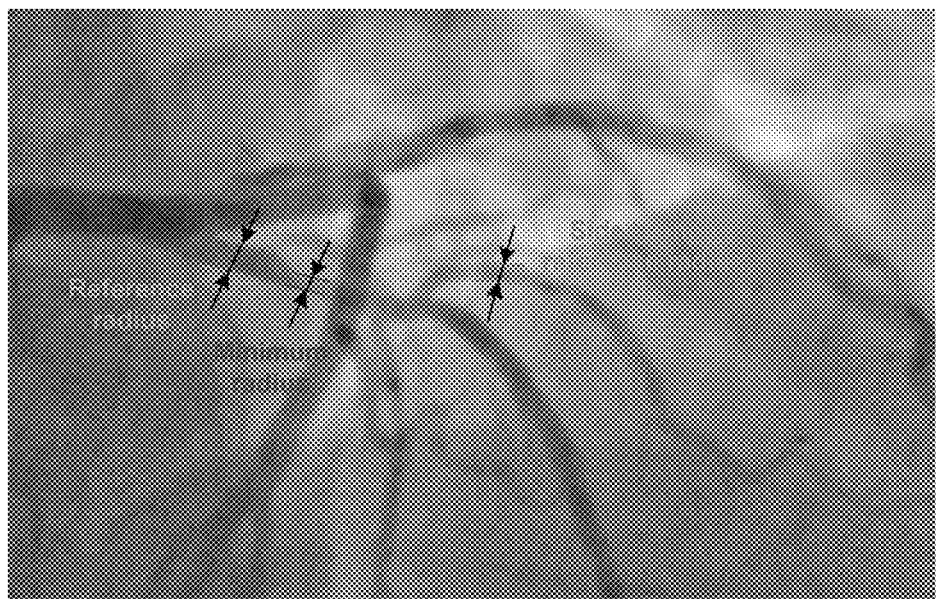
FIG. 24 is an example angiographic projection for two-dimensional vessel segmentation.

Any of the geometric features may be extracted directly from the medical images for application to patient-specific scan data. For example, radius information on a coronary tree is extracted directly from a two-dimensional projection, without having to reconstruct a three-dimensional vessel. FIG. 24 shows an example x-ray or angiograph projection image from which radii at various locations are extracted. The medical images may be processed, such as filtered, segmented, and/or masked, or not.

The medical image is a synthetic or artificial image generated from synthetic data. For example, the image is a rendering as a projection from a synthetic vessel geometry created from a model. For training, the synthetic image is used to extract features used for training. In other embodiments, the image is from a patient, such as by performing a medical scan of the patient. For application of the learned classifier, features are extracted from the image.

The feature extraction is performed on a medical imaging scanner or on another device, such as an imaging workstation. A processor performs the extraction with or without user input through a user interface having a display and user input (e.g., keyboard, mouse, trackball, touch pad, and/or touch screen).

The process of feature extraction from images is fully automated, semi-automated, manual, or a combination of thereof. Under a manual approach, anatomical or other features are input, annotated or measured by a human operator or user. For example, the user compiles a list of features required for a given hemodynamic metric (e.g., FFR) computation. The list is presented to the user on a display or the user obtains the list from another source. For example, an imaging scanner or workstation displays a dialog that the user can edit to insert the features. The user may alter the features on the list, such as adding, removing, or changing features. The user then assigns values to the features of the list. The image is used to determine the values for the features. The resulting list of values for the features is stored as part of the training database 28 or is used for application of the machine-learnt classifier.

In other embodiments, the user compiles a plurality of feature lists, each referring to different parts of the medical image. Each list may be associated to a different view of the anatomical structure of interest and/or a different spatial region. The user selects one or more parts of the image. For each selected part, the system provides a list of features. The user may edit the list and assign values to the features. The system combines the lists in a global feature list. The resulting combined list is stored or used for application. In alternative embodiments, the lists are maintained separately.

Figure 25:
FIG. 25 illustrates example annotation for distance.
Figure 26:
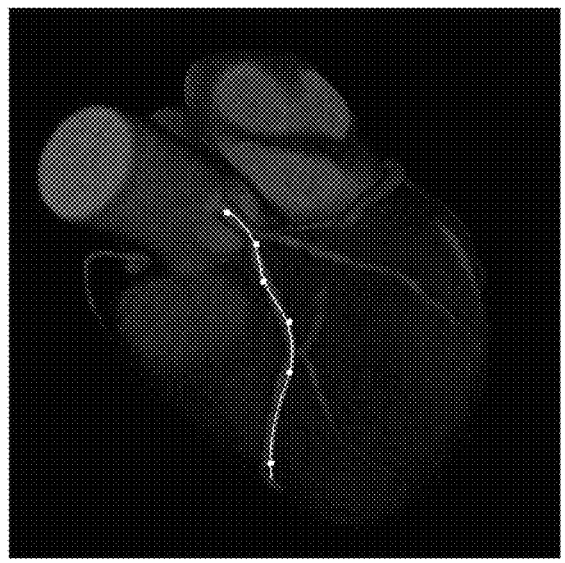
FIG. 26 illustrates an example annotation of a centerline.

To assist the user, the system automatically proposes one or more views of the anatomical structure of interest, cuts (e.g., segment or mask) parts of the medical image, and/or provides measurement tools that allow measuring geometrical features of the anatomical structure of interest. FIG. 25 shows an example annotation tool for measuring distance, such as a vessel length (left image) or vessel diameter (right image). A ruler allows computing Euclidean distance between points selected on the image. FIG. 26 shows an example annotation tool for tracing a centerline of a vessel or other structure. For example, the user clicks a number of points on the medical image, and the system draws a line connecting them. The system computes the length of a vessel along the curvilinear abscissa of the centerline.

Figure 27:
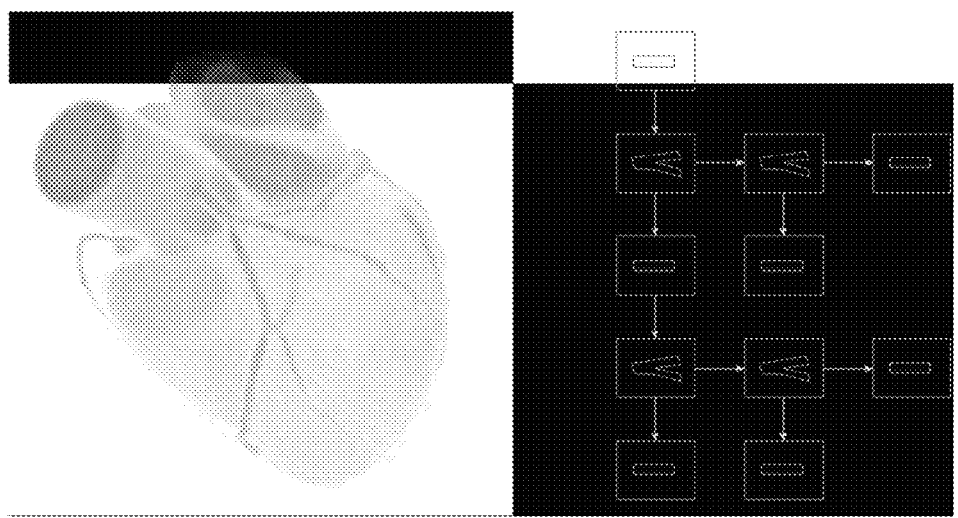
FIG. 27 illustrates example template options selectable for different synthetic representation of the anatomy.

Other annotation tools may be provided, such as the system providing a list of templates among which the user selects the ones that best represent the anatomical object(s) of interest (e.g. tapering vessels, bifurcations, trifurcations, and/or stenoses with different shapes). FIG. 27 shows an example tool for synthetic representation of the anatomy of interest for both creating the geometry as well as extracting features. The user chooses geometry templates and connects the templates to represent the whole anatomy. Each geometry template is labeled and color coded based on any feature (geometrical, hemodynamics, anatomical, and/or categorical). The geometry templates may be edited by the users (e.g. changing vessel radius, vessel length, vessel curvature, color code, or other characteristic). The list of features is automatically populated based on the selected geometry templates. The system may provide a same or different list of geometry templates for each part of the medical image and/or each view of the object of interest.

Under a semi-automated approach, some of the features may be extracted automatically by an algorithm, while some others may be annotated or edited, input, and/or corrected by the user. The system provides full or partial identification of geometry features of the arterial tree or of a subtree. The detected features may be shown on top of the medical image available for further user interaction or annotation. In one embodiment, anatomy is automatically detected by a processor. The user may edit and/or correct the detection results. The processor automatically computes the centerline and cross-sectional contours. The user may edit and/or correct the detection results. A list of features is displayed to the user. The user, interacting with the processor, inputs values or indicates the locations of measurements for processor determined values to be calculated. After any editing and/or correction by the user, the list or lists of features with corresponding values are stored or used in application.

Other embodiments with semi-automatic feature value determination may be used. One or more of various options or differences are provided. The system performs jointly the automatic detection (e.g., myocardium, coronary ostia, and/or main branches) and computation of centerline and cross-sectional contours. The user edits the centerline and the cross-sectional vessel contours by interactively changing their position and/or shape on the medical image. The user creates new centerline branches and additional contours besides the ones automatically generated by the system. The system populates the list of geometric features using both the ones automatically detected and the ones manually added by the user. The system keeps track of the features currently added to the list and prompts the user to add missing features, if any. The system has a pre-defined ranking of features, based on their effect on the final computed value, and the list of features is shown color-coded based on this ranking. One possible application of this is user guidance during feature identification so that the user may make sure that the most relevant features are carefully captured. The system computes the hemodynamic metric of interest continuously as features are being added to the list, and interactively shows the resulting value or the metric's sensitivity to the current feature being added.

In one embodiment, the system displays suggested ranges for each feature, based for instance on databases, population averages, literature search, previous data from same patient, or other source. The system compares the current list of features with reference values from any source and prompts the user to correct and/or confirm features if the computed value is outside expected or suggested ranges of variations. The system automatically proposes a selection of geometry templates representing the anatomical object of interest. The system displays suggested ranges for the parameters of the geometry templates, based for instance on databases, population average, literature search, previous data from same patient, or other source. The system automatically fills the list of features, and prompts the user to edit, add, and/or correct the list. When the user adds or edits a feature, all or part of the other features are updated accordingly. Additional, different, or fewer variations for semi-automatic extraction of values of features may be provided.

Figure 29:
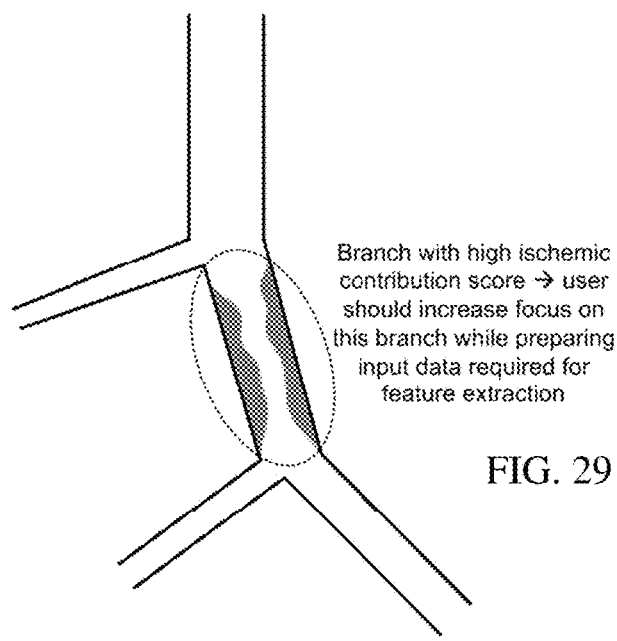
FIG. 29 shows an example segment with a high ischemic contribution score.

Furthermore, the feature values may be used to indicate for the user on which part of the geometry to focus when providing manual input for the extraction of features. For example, if the ischemic contribution score of a certain branch is high, then the user should focus on that specific branch when providing input information (e.g. when segmentation is performed). FIG. 29 shows an example of a branch with high ischemic contribution on which the user should focus while preparing the data required for feature extraction.

Under a fully-automated approach, an underlying image-processing algorithm first detects the anatomical region of interest. For example, the algorithm automatically detects the stenosis, coronary vessels, coronary ostium, cardiac chambers, myocardium, trabeculae and papillary muscles, and/or aorta. Next, the algorithm extracts anatomical features from the medical image in the detected regions. The system provides fully automatic detection and quantification of the features for the computation of the hemodynamic index of interest. The result of the automatic approach is a complete list of features with populated values. The collection of geometry or other features thus identified may or may not be enough to reconstruct an accurate three-dimensional geometrical model.

Referring again to FIG. 2, values of the hemodynamic metric or metrics of interest are determined in act 16. A value for the flow characteristic is determined and stored for each of the examples of the vessel arrangements in the synthetic data. The value of the flow is the ground truth used for training the classifier. The values are stored with the feature for each example in the database 28.

The machine learning maps the input features to a value or values of one or more hemodynamic metrics. Any hemodynamic metric may be used. The metric is for a part of the vessel structure or for the overall vessel structure of interest. Various example metrics include pressure (e.g., average, instantaneous, time-varying, wave-free interval, averaged over a certain sub-interval of a cardiac cycle, or other), flow rate (e.g., average, instantaneous, time-varying, wave-free interval, averaged over a certain sub-interval of a cardiac cycle, or other), wall shear stress (e.g., average, instantaneous, or other), oscillatory shear index, vessel wall strain, vessel wall stress, or any combination of the above defined by any mathematical operator (e.g., addition, subtraction, multiplication, division, integral, derivative, or other). Example hemodynamic metrics specifically for the coronary computations include fractional flow reserve (FFR), instantaneous wave free ratio (iFR), ratio of average distal pressure to average proximal pressure (basal Pd/Pa), basal stenosis resistance (BSR), hyperemic stenosis resistance (HSR), calcium score, risk of plaque rupture (e.g., separately for each type of tissue: fibrous tissue, lipid tissue, necrotic tissue, and calcified tissue), endothelial dysfunction, or any combination of thereof.

The hemodynamic metric value or values are extracted for each of the synthetic examples used in the training data and used for extracting features. The geometric and other features are determined for each setup for example, and, together with the hemodynamic metric values, the features and values are used to populate the training database. Based on the representation of the synthetic models (e.g., in vitro or in silico), different methods may be used for extracting the hemodynamic metric required during the training phase. Flow simulation and/or experiments are used for the in vitro model. Flow computation, such as based on computational fluid dynamics, is used for the in silico models.

Figure 28:
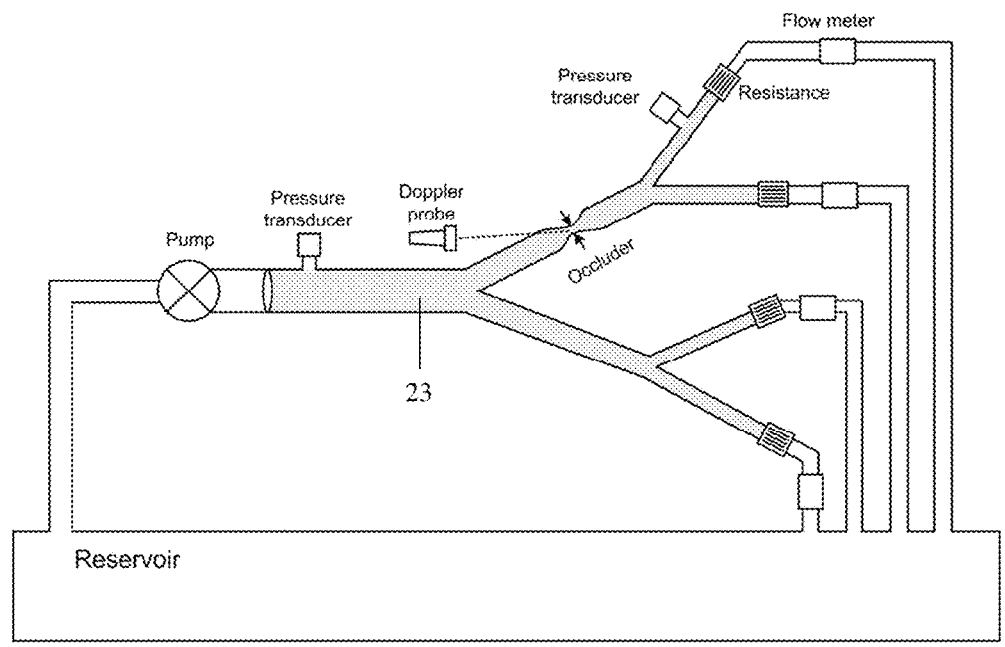
FIG. 28 illustrates one example of an in vitro model for generating synthetic data.

For the in vitro models, the hemodynamic metric is determined based on measurements during a simulation. The pressure, flow, velocity, or other hemodynamic information used to calculate the value of the hemodynamic metric are measured. FIG. 28 shows an example in vitro model 23. The model 23 includes tubes or other material simulating a vessel. The shapes of the tubes or by shaping the tubes, the various geometries of the vessel may be established. The simplified model 23 of FIG. 28 includes an in vitro vessel tree is modeled with tubes, a pump circulates a fluid, with properties similar to the ones of human blood, through the in vitro model 23, hydraulic resistances (i.e., flow restrictors) couple to the terminal in vitro segments to generate realistic levels of pressure inside the in vitro model, a reservoir for collecting the fluid, one or several occluders for generating constrictions in the in vitro model, and one or more measurement devices (e.g., pressure transducers, flow meters, Doppler probe for measuring velocity, and/or other sensors) used to determine the hemodynamic metric. Additional, different, or fewer devices may be provided, such as joints or clamps for altering branch locations and/or the number of segments.

The in vitro model 23 and the flow conditions may be modified in numerous ways to generate a large number of setups. For example, the number, position and shape of the occluders is altered. As another example, the resistance at one or more locations is altered. In yet another example, the operation of the pump is altered. The number of side branches and any occlusions may be altered. Other alterations of combinations of different alterations are used to create different models with corresponding features and resulting flow characteristics. These alterations are used to populate the database with synthetic examples including the extracted features and hemodynamic metric value or values for each of many models 23.

For in silico models, there is no experimental table-top set up to measure flow. Instead, computational flow dynamics (CFD) or other flow modeling is used. Any computational approach for modeling the flow of blood in the human cardiovascular system may be used. Models with different complexities and scales have been proposed, ranging from lumped (or zero-dimensional-models), one-dimensional models, two-dimensional models, and three-dimensional models with rigid or compliant walls (e.g., fluid-structure interaction models). The nonlinear partial-differential equations of these models are solved with finite difference methods, finite element methods, finite volume methods, spectral element methods, boundary element method, Lattice-Boltzmann method, other methods, or combinations thereof. For specifying the boundary conditions required for performing blood flow computations in the synthetic geometries, personalized boundary conditions (e.g. using allometric scaling laws based on vessel morphology) or generic boundary conditions may be used. Steady-state and/or transient flow computations may be used. When personalizing the computations based on allometric scaling laws, the personalization may refer to any flow state, such as rest, hyperemia or exercise.

Compared to an in vitro setup, for a single synthetic case for in silico modeling, each location of that case may be used for generating a feature vector in the training database. Moreover, for each synthetic case, different flow conditions may be imposed and separate feature vectors may be extracted for each flow condition.

Referring again to FIG. 2, machine learning trains the classifier in act 14. The input feature vectors and corresponding values of the flow characteristics for many vessel arrangements are used in machine learning. Tens, hundreds, or thousands of examples are generated synthetically. The corresponding feature values and hemodynamic metric values are used to map the feature values to the metric values. Once the features and the hemodynamic metric of the synthetic vessel trees have been extracted, the next step is to train a machine learning algorithm for predicting the hemodynamic metric.

Any type of machine learning algorithm may be used. The machine learning is supervised, semi-supervised, or unsupervised. Some examples using supervised learning include regression, instance-based methods, regularization methods, decision tree learning, Bayesian, kernel methods, clustering methods, association rule learning, artificial neural networks, dimensionality reduction, and ensemble methods. Probabilistic boosting tree, hierarchal, or other processes may be used.

The machine learning may use all of the input features. Alternatively, the machine learning determines discriminative features and selects a feature set to be used for classifying. A subset of the extracted features may be used for learning, as determined from feature selection and ranking, feature combination, or other process.

More than one classifier may be created. Since different types of branches and regions are present in a vessel tree, different classifiers may be machine trained for the different branches and/or regions. For example, different classifiers are trained for main and side branches, bifurcation regions and single branch regions, different types of pathologic regions such as different types of single branch stenotic regions (e.g., focal, long, diffuse, restenosis, or other), different types of bifurcation stenoses (e.g. a separate model for each bifurcation stenosis type in the medina classification), different types of aneurysms, different types of plaque, different types of total and/or sub-total occlusions, stenotic and regurgitant valves, various pathologies of the heart (e.g., past infarct or myopathies), or different types of branches (e.g. in case of coronary arterial trees: LM, LAD, LCx, RCA, Diagonal, OM, or other). Since the training is based on synthetic geometries, a large enough number of training instances may be generated for each of these different classifiers. Another possibility is to divide the geometry into separate segments (e.g. for coronary geometries: proximal LAD, mid LAD, and distal LAD) and to extract the features discussed in the previous sections separately for each segment. Afterwards these features may either be combined into cumulative features or used separately for a single or multiple machine learning algorithms for predicting a hemodynamic metric of interest.

Once trained, the machine-learnt classifier is instantiated as a matrix or matrices. The matrix maps the values of the input features to values of the hemodynamic metric. This mapping is used to predict the hemodynamic metric in 22. In this prediction phase, features are extracted from patient-specific data in act 20. These patient-specific features are input to the machine-learnt classifier, which outputs a value or values for the hemodynamic metric. For example, based on the features extracted from a medical image of a scan of a patient, the trained model is applied to compute FFR for that patient.

The machine-learnt classifier may be used in a feedback approach. While performing preparatory steps to extract additional features and/or features for other parts of the vessel, intermediate results may already be computed using the machine learning algorithm and displayed to the user. This may potentially give useful feedback for obtaining the final results. FIGS. 30A and 30B show an example. FIG. 30A shows an example of a partially processed geometry for which the hemodynamic metric may be predicted and displayed. FIG. 30B shows the workflow used in this case, which contains a loop in order to continuously generate new predictions while the input data is being processed in act 52. This approach is feasible due to the fact that the prediction of the hemodynamic metric from a set of features is almost instantaneous.

Rather than training one classifier, the classifier may be learned as a network of different models, where each model works on some subset or the entirety of the feature space. The outputs from each model may be used as inputs to other models, thereby creating new features. As one example, the output of upstream nodes may be used as a feature to predict required quantities at downstream locations, and this procedure may be applied iteratively to reconstruct the quantity on the entire arterial tree. The output from one model may be used as an input to the same model to produce recursive model estimates. The classifier may be trained to learn from categorical, discrete, and/or continuous features. The predictive classifier may be a combination of multiple interacting machine-learnt classifiers, each of which use the same or a different subset of features.

Once trained, the machine-learnt classifier or classifiers are used to predict. To predict the flow for a specific patient, medical scan data representing the patient is acquired. The scan data is acquired by a medical scanner and represents the vessel structure of the patient. For example, the medical scan data is angiogram data. Computed tomography, magnetic resonance, ultrasound, PET, SPECT, x-ray, combinations thereof, or other type of medical scan data may be acquired. In alternative embodiments, the scan data is acquired by upload from a memory or receipt from a transmission. The scan data is specific to a given patient, so is from a scan of that patient rather than synthetic data.

The medical scan data represents a three-dimensional region of the patient. A set of scan data representing intensity at different voxels distributed over three dimensions is provided. In other embodiments, the medical scan data is a zero, one, or two-dimensional representation of the vessel structured. Two or three-dimensional scan data is processed to create a zero, one, or two-dimensional representation of the vessel structure of the specific patient.

For prediction, features are extracted from the medical scan data. Features may be extracted from other data for the patient as well. Similarly, replacement features may be provided for features that are not available for a given patient, such as using an average value.

The approaches discussed above are used to extract the values from the medical scan data and other data for the specific patient. The entire set of features from patient data during prediction is extracted and then the machine learning algorithm is used to predict a hemodynamic metric. The preparation of the data for extracting the features uses manual, semi-automatic, or automatic approaches. For a patient dataset, where some hemodynamic parameters are to be computed, the relevant features are extracted from the patient images and then applies as inputs to the learnt machine learning model.

The features selected by the user are from either the same view, or from different views of the anatomy. The features may also be selected from multiple imaging modalities. As an example, if the patient has a pre-operative CT scan, some features are selected on the CT scan and some on the intraoperative angiographic acquisition. These additional images may be from any modality, including but not limited to MRI, CT, X-ray angiography, intravenous ultrasound (IVUS) and optical coherence tomography (OCT). The features may contain information about past history of the patient. For example, some of the features are related to stents already in the patient from past percutaneous coronary intervention (PCI) procedures. If the patient suffers from a severely enlarged heart, has myocardial scarring from a past infarction, or other condition, this information may be used as a feature. The predictive classifier is adapted to take account of this feature and increase accuracy. The features are extracted directly from the medical image or from a processed representation of the medical scan data. The processed version may be a mesh, a mask or probabilistic descriptors of the presence of different anatomical features.

In act 22 of FIG. 2, the extracted feature values are input to the machine-trained classifier. A processor inputs the values as part of application of the classifier. The machine-trained classifier is trained only from synthetic data or from a combination of data from a collection of patients and synthetic data. For synthetic data, the machine-trained classifier is trained from examples of vessel arrangements generated with computer modeling, physical modeling, or both computer and physical modeling using the in vitro or in silico models and corresponding ground truth hemodynamic measurements or computations. The features extracted from the medical scan data of the patient for application in act 20 are input to the classifier.

As a result of the input, the processor outputs the value or values for the hemodynamic metric. The processor applies the machine-trained classifier to determine the flow. The flow is output as a value, graph, annotation, display, or image.

The predicted quantity is any hemodynamic quantity, including but not limited to pressure, velocities and quantities derived from therefrom. For example, the surrogate model predictions are FFR, iFR, CFR, BSR, HSR, basal Pd/Pa, pressure gradients or another quantity. Flow rates, shear stress, time integrals of these quantities, likelihood of plaque rupture, classification of the nature of plaque, or other metric may be predicted. More than one metric may be predicted.

The predictions are continuous variables, such as the pressure or related variables, or categorical variables, such as a discrete prediction of the presence or absence of disease or a discrete grading of the severity of disease. The predicted indices may be either cycle-averaged quantities or transient quantities, showing the systolic and diastolic variation.

Further, model predictions may be used to infer organ perfusion and to predict parts of the organ that may be vulnerable. The model predictions may also be used in combination with other imaging data, such as perfusion and stress echo, to improve the image as well as to identify further features.

In one embodiment, the one or more predicted values are output on a display with an image of the vessel structure generated from the medical scan data. Computed hemodynamic indices may be displayed interactively to allow changes in the feature set. If the user choses to alter the value of any feature, the resulting value is reflected in the value of the computed indices at all points. The model predictions may also be shown as a ranking of the most severe pathologies, where intervention could have the most beneficial impact for the patient. For the coronaries, the model may order the lesions in decreasing order of severity. Once one of the lesions is stented, the model may immediately update the hemodynamic indices, such as FFR, and reorder the remaining lesions according to the new predictions.

The predictions from the model may be used to guide the placement of interventional devices such as catheters, pressure wires and for stent deployment. The predictions may be used to ascertain that the stent has been placed in a manner providing optimal benefit to the patient. The interactive nature provided by the efficient prediction from features makes it possible to immediately update the predictions as soon as a stent is placed to confirm if the deployment is successful.

In one example output, computed FFR results are visualized on a display of the medical scanner or on another device, such as an imaging workstation. A medical image, such as an angiogram, is displayed. Any point on the image may be queried (e.g., point and click) for the associated metric, and the corresponding metric value is shown overlaid to the image. FIG. 31 shows an example where the user selects a point on a root of the vessel structure. As an example, points of interest in the coronary tree are selected, and the corresponding FFR value is shown in the image as demonstrated in FIG. 31. The user may activate a "no click" mode, in which case the value of interest is displayed in correspondence of the cursor by just positioning the cursor on the position of interest.

By displaying the value of the metric, other interactions with the user may be provided. For example, the system provides a touch screen enabling interactions with the anatomical object of interest, such as gestures to rotate, zoom, and pan. Point and touch causes the system to display the value of interest at the point of touch. As another example, the system provides an eye-tracking device, so that the value of interest is displayed at the location that is being observed by the user.

Rather than displaying a two-dimensional image or a rendering from three-dimensional medical scan data, the arterial tree is represented on the display as an abstract graph or tree. The graph may be color coded based on the features of interest. The system may automatically synchronize the traversal of the schematic with the traversal of the image for point-to-point correspondence.

Figure 32:
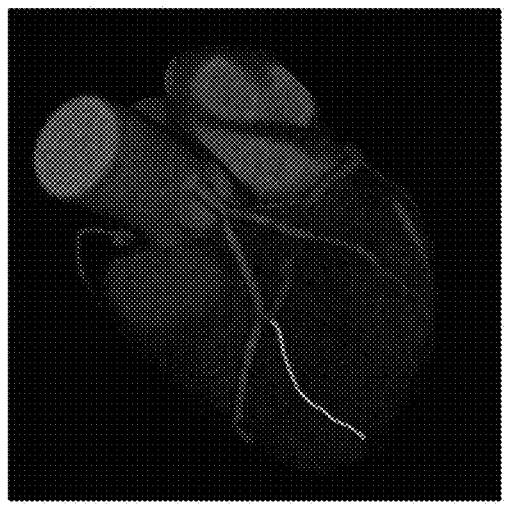
FIG. 32 is an output according to one embodiment with color coding.
Figure 32:
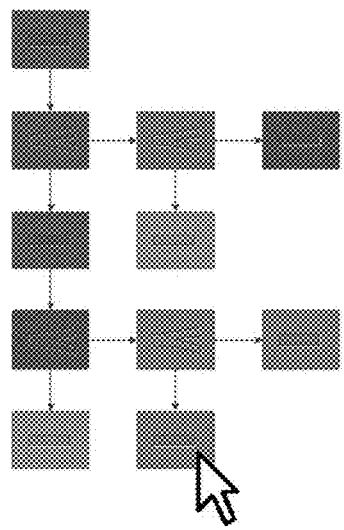

Other outputs of the hemodynamic metric value for a sub-part or less than all of the vessel tree may be used. FIG. 32 shows one embodiment where a synthetic representation of the anatomy of interest is color coded based on the hemodynamic index of interest. The system synchronizes the traversal of the image with the traversal of the diagram.

By selecting an extracted, coded representation or by selecting the coded part of the image, the corresponding metric value or values are output.

Figure 33:
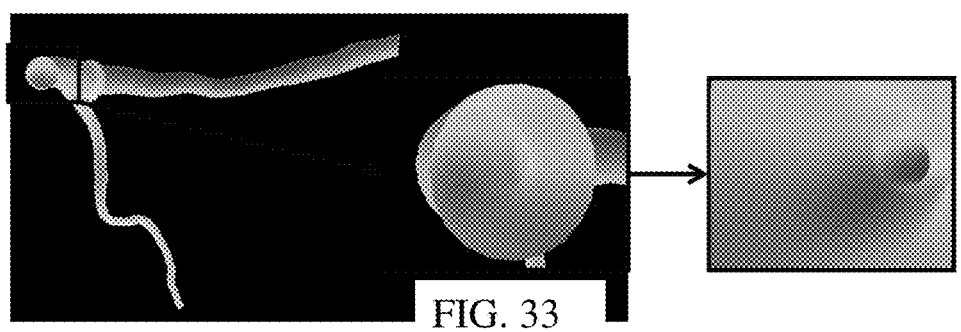
FIG. 33 is an example fly-through visualization.

FIG. 33 shows another example output. Based on the extracted features or geometric structure, the arterial tree is represented as a three dimensional structure that can be visualized and interactively navigated in a fly-through mode. A similar synthetic three dimensional structure may also be color coded based on the features of interest. The vessel surface may be color-coded based on any quantity of interest.

Figure 34:
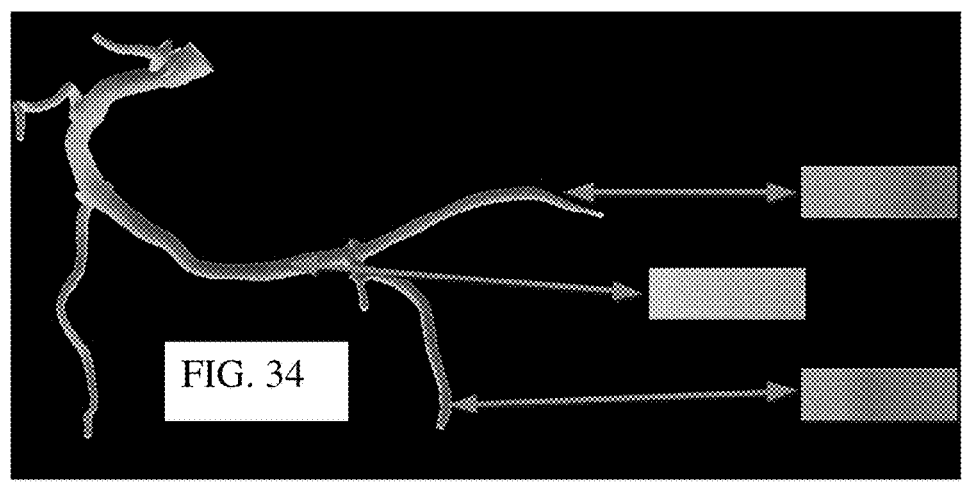
FIG. 34 is an example unfolded view of the vessels in an arterial tree.

FIG. 34 shows yet another example output. Each vessel is mapped to a plane and represented "unfolded." In this view, the coronary tree looks like a two-dimensional tree. Each vessel may be color coded by the feature or metric value of interest. In this representation, additional information on the vessel is also visualized (e.g. endothelial function, wall shear stress, or plaque burden).

In another embodiment, the coronary tree is mapped to an atlas or a pictorial representation of the anatomical structure. The image is color or otherwise coded based on the value of the feature or metric of interest. The system provides an automatic synchronization of the navigation of the atlas and the image.

Figure 35:
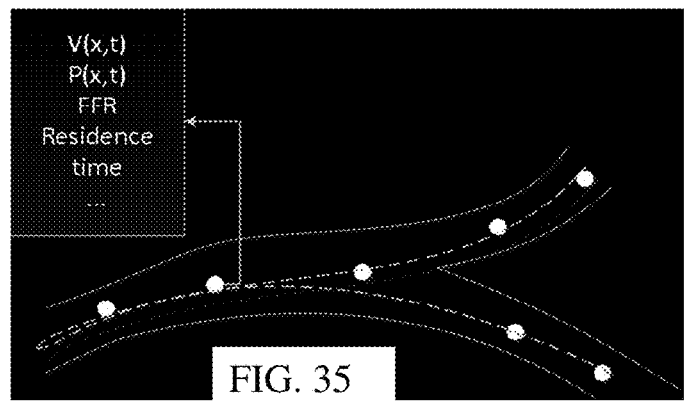
FIG. 35 is an example output where particles are represented with statistical information.

FIG. 35 shows another embodiment of an output. Any feature or metric of interest is represented by showing one or more particles (glyphs) moving (or fixed) along the centerline (or more generally inside the image). The points are color or otherwise coded based on feature or metric value of interest. The same particles (glyphs) may be associated with the statistics of the features or metrics of interest, evaluated at the location of the particle. By selecting the particle, the statistics or values are shown.

Figure 36:
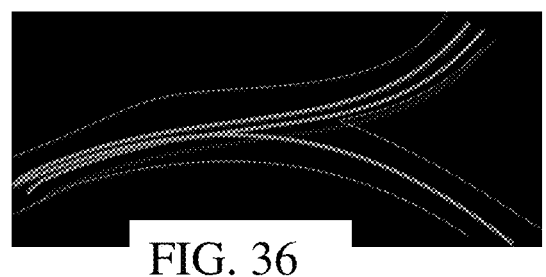
FIG. 36 is an example vessel visualization for different hemodynamic metrics on a path inside the vessel.

FIG. 36 shows another embodiment of the output. A path (represented as a line) in the vascular tree is shown and color-coded based on the value of the feature or metric of interest. Either same or different paths may be determined for different features.

Figure 37:
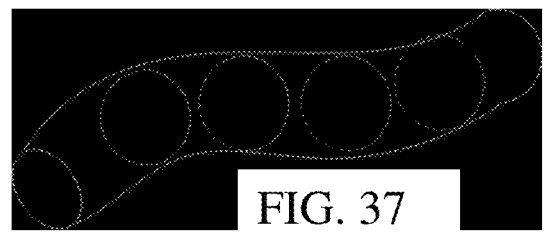
FIG. 37 is an example vessel visualization with cross-section information.

FIG. 37 shows another output. The vessel is represented as a three-dimensional rendering with different cross-section markers. The cross-section markers are color or otherwise coded based on the value of the feature or metric.

In other embodiments, flow pathlines or streamlines are added and color coded based on the value of interest. The image of the coronary tree may be color coded based on any feature extracted during the pre-processing phase, based on any computed feature, or based on the predicted metric value. As an example, the computed FFR value is used to color the coronary tree.

Figure 38:
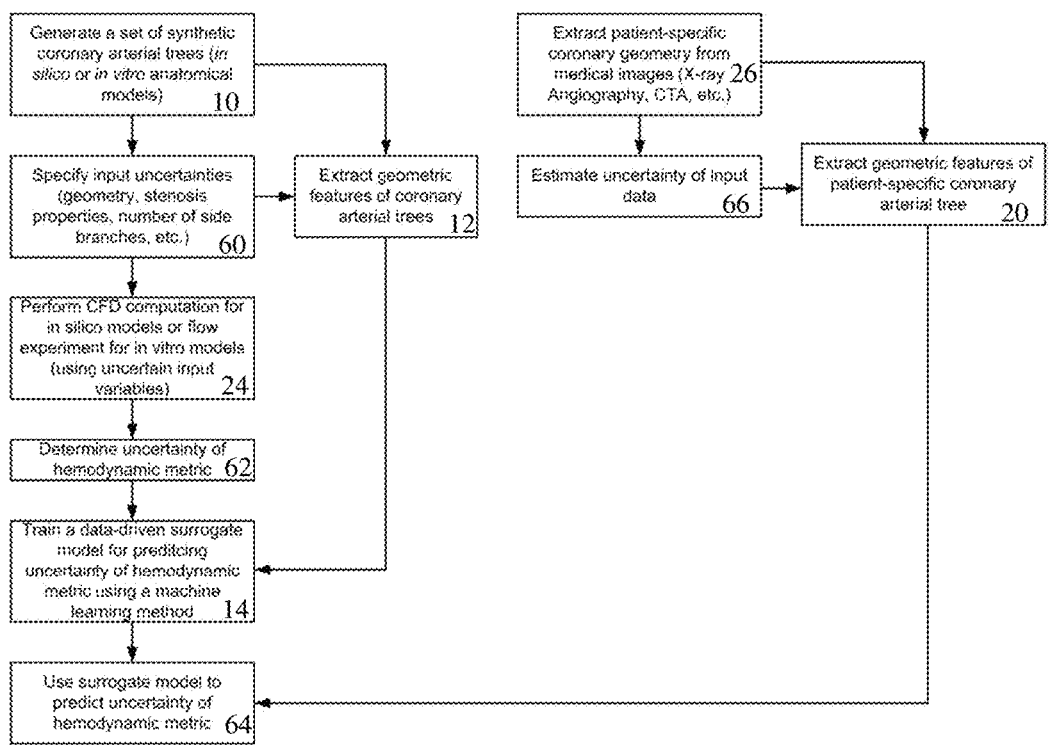
FIG. 38 is a flow chart of one embodiment of a method for hemodynamic determination in medical imaging using uncertainty.

FIG. 38 shows another embodiment of the overall process of FIG. 2. Acts 60, 62, 64, and 66 are added for dealing with uncertainty. In act 60, uncertainty is assigned to one or more features. The uncertainty is a distribution of possible values for the feature. For example, the radius may be measured as 0.25 cm, but the accuracy or tolerance in the measurement provides that the radius is between 0.20 cm and 0.30 cm with greater probability for the values closer to 0.25 cm. Any distribution of possible or probable values may be used, such as a normal distribution, a distribution from a study, or from another source.

The distributions for a set of one or more uncertain input variables is used in forming the synthetic data. In one example, the confidence intervals are obtained during the training phase by stochastically perturbing the synthetic geometry to obtain a range of predictions. Synthetic examples for each of the possible values are created. As a result, the machine-learned classifier may output the resulting ranges or distribution of metric values given the uncertainty in the feature value. The uncertainty is propagated through a forward model, and the uncertainty for the hemodynamic metric is determined. Alternatively, the uncertainty of the metric value is learned through a machine learning algorithm based on the extracted features with the distribution reflecting uncertainty of the feature value used as an input.

For prediction, the same features are extracted for a patient-specific geometry and uncertainty in the input data is specified either automatically or by the user. The user may input or select the distribution. Using the machine-learnt algorithm, the confidence of the estimated hemodynamic metric is provided. A confidence or probability is provided for one value of the metric. Alternatively, the predictions from the learnt model may also be ranges or confidence intervals within which the predicted quantity is expected. The predicted confidence interval for the patient could be either directly predicted from the model or estimated from a set of similar anatomies from a saved database of synthetic models.

A graph representing the distribution of values of the metric given the uncertainty is output. Any expression of the confidence interval as a distribution of different values of the metric resulting from the distribution of the input values for a given feature may be used. The output hemodynamic metric includes a confidence or confidence interval of different values of the metric resulting from the uncertainty in values of one or more of the input features.

In another embodiment, automatic adaptation is provided. Online machine learning is used where feedback about accuracy of one or more predictions are used to add non-synthetic examples to the database 28 so that repetition of the machine learning may result in a more accurate classifier. The system is capable of including the effects of known measurements. If the measurement of a hemodynamic parameter for a given patient is provided at any location, the system uses this information to improve the accuracy of any subsequent predictions. Further, the error in the original prediction at the location where data is provided may be used to improve the mode's future performance. In alternative embodiments, the machine-trained classifier is used without feedback or update.

For feature extraction, the users' corrective actions taken to improve automatically identified features may be used to improve the feature detection in the future. The system learns from the user inputs. The improvement for feature extraction and/or adaptive learning for the classifier may be on a global manner or a site-specific manner. This allows the system to account for anatomical trends based on patient demographics.

Other adaptation of the machine learning may occur. If measurements of the hemodynamic metric become available, the system may automatically or semi-automatically identify outlier cases or cases where the value of the metric is with a given standard deviation of the norm. These cases are then used to create a new set of synthetic geometries that mimic the features of the outlier, together with the already available training set to improve the model predictions. With the updated database 28, the classifier is trained again.

In addition to anatomy, if flow measurements are also available (e.g. Doppler), then the measurement values are incorporated in the machine learning approach as ground truth for a given example. The training data is updated with new features characterizing flow as inputs. In the prediction phase, if the measured values of these 'flow' related features are available, these flow features are used as inputs in the feature vector. In the absence of flow features, similar patients or similar models to the patient are located in the database from the geometric features to arrive at data-driven estimates of flow in different branches. This flow is used as a substitute feature for prediction.

Figure 39:
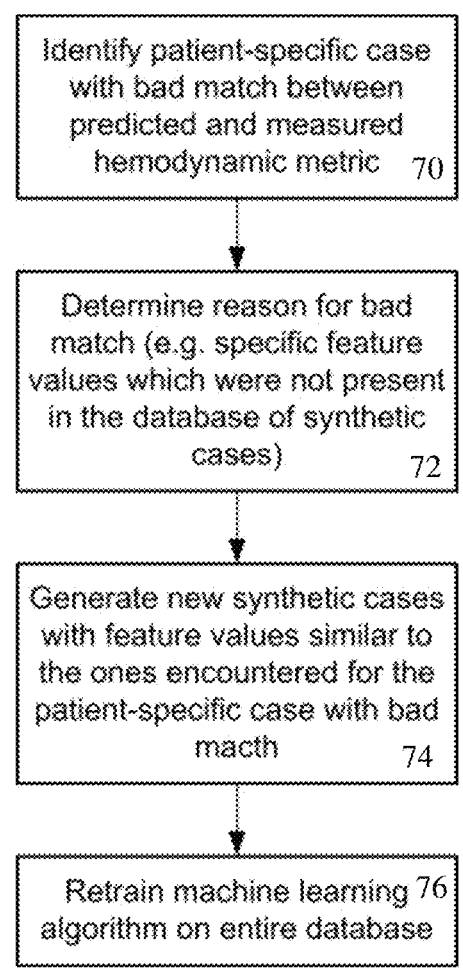
FIG. 39 illustrates one embodiment of a method for updating synthetic data and a machine-learnt classifier.

Although a very large number of synthetic cases may be generated for training, the examples will not cover all patient-specific cases. Hence, when using the machine-learnt classifier to predict results for patient-specific data, bad matches between predicted and measured hemodynamic metrics might appear while validating the machine-learning classifier. In this case, the workflow displayed in FIG. 39 is used to enrich the database of synthetic cases so as to improve the prediction for the patient-specific cases that lead to a bad match. The process displayed in Error! Reference source not found. may also be performed directly on the workstation since the generation of synthetic cases may be fully automated. In act 70, the case with the bad match is identified. A distance of the feature vector from the feature vectors of the examples is used to identify a bad match. Alternatively, the predicted value is compared with a measured value to identify the bad match. In act 72, the reason for the bad match is found. The reason may be feature values not present, the feature values that are most different, and/or the feature values most determinative of the flow value. In act 74, new synthetic examples with similar features are generated and added to the database 28. The value of the hemodynamic metric for the added examples are computed or measured. In act 76, the machine learning is performed again with the updated or adapted database examples.

In another embodiment, sequential machine learning is used. A sequence of machine-learnt classifiers is created. For example, a hemodynamic metric is predicted from geometrical features. That value and other features are used to predict the same metric using a different classifier. Any hierarchy of classifiers and corresponding machine training may be used.

Figure 40:
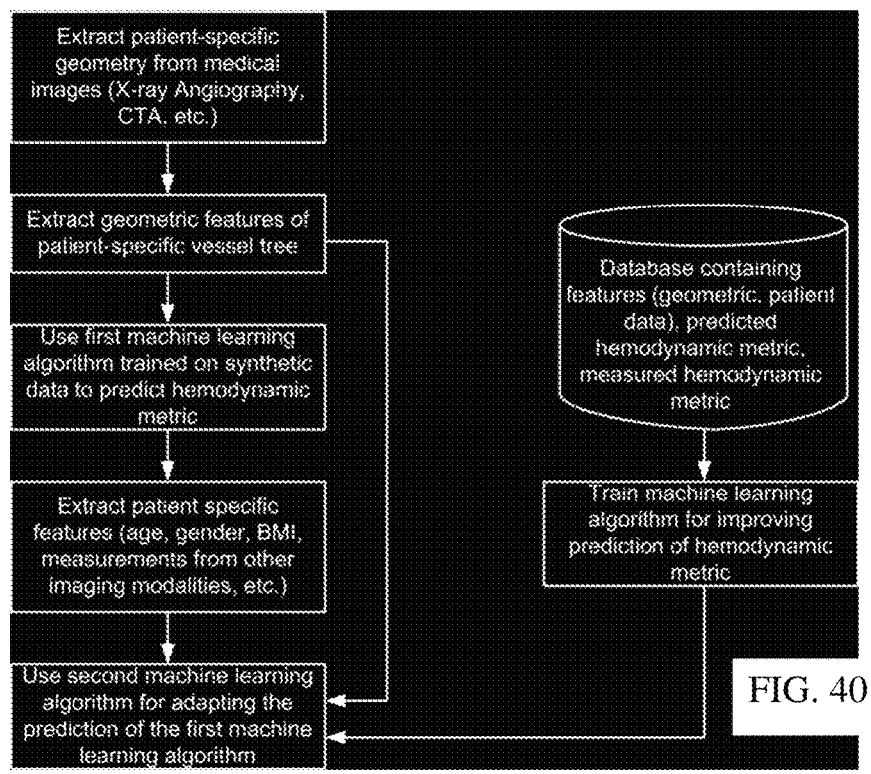
FIG. 40 is a flow chart of one embodiment of a method for hemodynamic determination in medical imaging using sequential learning.

In one example, the first machine-learnt classifier is trained with completely synthetic data during the training phase. The result predicted by the machine-learnt classifier for a patient-specific input feature vector may be improved by using patient characteristics. FIG. 40 shows improvement using a sequence. First, the geometry is extracted from patient-specific medical scan data in act 26, and features are extracted from the vessel geometry in act 20. A flow metric is predicted in act 22 by the classifier trained on purely synthetic data. In act 78, further patient-specific features are extracted, such as age, gender, BMI, measurements from other imaging modalities, or other information. In act 80, a second machine-learnt classifier uses the result predicted by the first classifier as feature, alongside the patient characteristics, in order to improve the final prediction. The database used for training the second machine-learnt classifier may use non-synthetic data, such as data from application of the first classifier on actual patients where the patient-specific flow is measured and used as a ground truth.

Any features may be used for the subsequent classifier. For example, left or right dominance in case of coronary circulation, type of lesion specified as described for example in the syntax score (e.g., coronary segment with lesions, type of lesion, medina grading for bifurcation lesions, bifurcation angle, ostial lesion, tortuosity, length of lesion, calcification, thrombus, diffuse disease, or other measure), patient demographics (e.g., age, gender, BMI, height, mass, smoker/non-smoker, or other), pathological history (e.g., presence of hypertension, presence of hyperlipidemia, diabetes mellitus, angina type (stable/unstable/silent), previous cardiovascular history (stroke, infarct, PCI, stent, CABG, etc.), non-invasive stress tests (e.g. stress echo), peripheral vascular disease, kidney disease, exercise ECG—stress test, exercise radioisotope test (nuclear stress test, myocardial scintigraphy)), blood biomarkers (e.g., hematocrit, lipoprotein level, triglyceride, or other), medication used in the past or present (e.g., aspirin, Beta-blocker, Nitrate, Statins, ACE inhibitors, Calcium-channel blockers, or ARBs), measurements extracted using any imaging modality (e.g., MRI→blood velocities, blood flow rates, movement of arterial wall; Doppler blood velocities; IVUS→plaque characteristics, lumen information, eccentricity of lesions; angiography→contrast agent propagation; and/or echocardiography→myocardial characteristics like myocardial strain), invasive measurements from catheterization (e.g., invasive pressure, flow, and/or resistance measurements at any location in the cardiovascular system), other measurements, or combinations thereof. Any feature from the first phase of the sequential approach may be removed from that phase and used only during the second phase.

The sequential machine learning approach may also be used to predict the future evolution of the patient. For example, the geometric features together with the predicted hemodynamic metrics and any other feature listed above may be used for predicting the risk of restenosis. The second classifier is in this case trained on patient evolution data acquired in the past.

One possibility is to build a database with the patient-specific data of previous cases and to use this database during the training of the sequential or second classifier. As described before, during the first step, the classifier learned on synthetic data is used to generate a first prediction of the hemodynamic metric. During the second stage, the features extracted for the patient-specific data are used to find similar cases in the patient database and a second machine learning algorithm is applied for predicting the final value of the hemodynamic metric.

In yet another embodiment, the machine-trained classifier is trained for therapy planning. Any of various therapies for the vessel may be performed, such as stenting, cauterizing, cutting, resection, grafting, drug exposure, or other procedure. The therapy is performed to have a hemodynamic effect. The classifier may be used to predict the hemodynamic metric by type, location, and/or amount of therapy.

Figure 41:
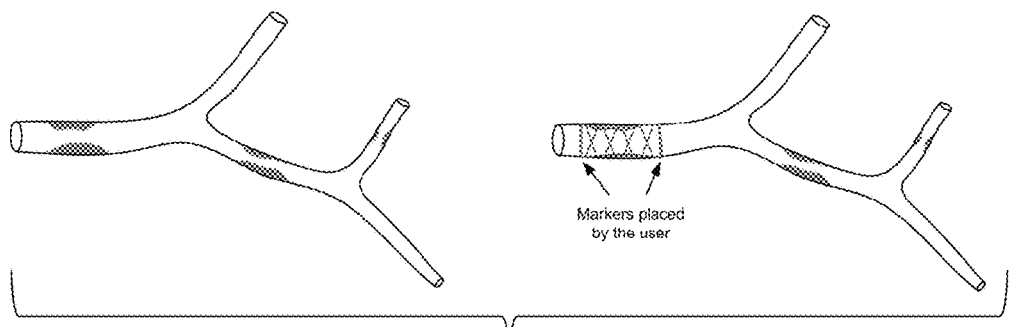
FIG. 41 illustrates modification due to virtual therapy.
Figure 42:
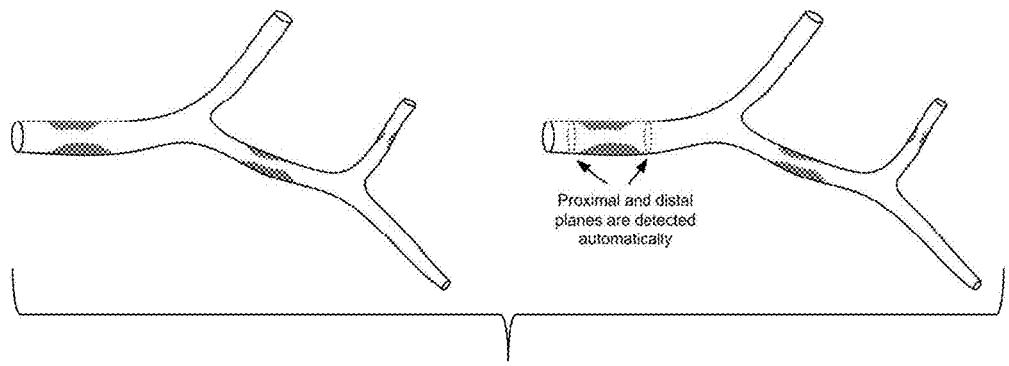
FIG. 42 illustrates automatic detection of proximal and distal planes of a stenosis.

Similarly, the classifier may be used to determine which of various abnormalities to treat. The classifier is used to assess the hemodynamic effect of individual lesions in a vascular tree. FIG. 41 shows a coronary tree with three stenoses. The same approaches and workflows may be applied to other vascular pathologies. To assess the effect of each stenosis and thus to determine which stenoses may require PCI, various approaches may be used. In one approach, the user marks the stenosis to be treated. The geometry is modified so as to reflect the placement of a stent whose size and positioning is chosen by the user. FIG. 41 shows the resulting change in geometry. In another approach, the stenoses are automatically detected. FIG. 42 shows detecting of proximal and distal planes defining the stenosis. The hemodynamic metrics are adapted so as to remove the effect of each stenosis on the hemodynamics. The initial geometry does not have to be modified, but instead the metric value is altered.

Although straight-forward from an algorithmic point of view, the first approach has the disadvantage of relying on extensive user interaction. The stenosis is identified, a stent size is chosen, and the effect of stent placement on the geometry is assessed, all by the user. The second approach is fully automated and the user only needs to select the stenosis whose effect on the hemodynamic metric needs to be assessed. For the second approach, the classifier used for assessing the hemodynamic metric has to be modified. If a blood flow modeling approach is used, the pressure drop model may be modified so as to reflect the effect of a stent on the hemodynamics.

Figure 43:
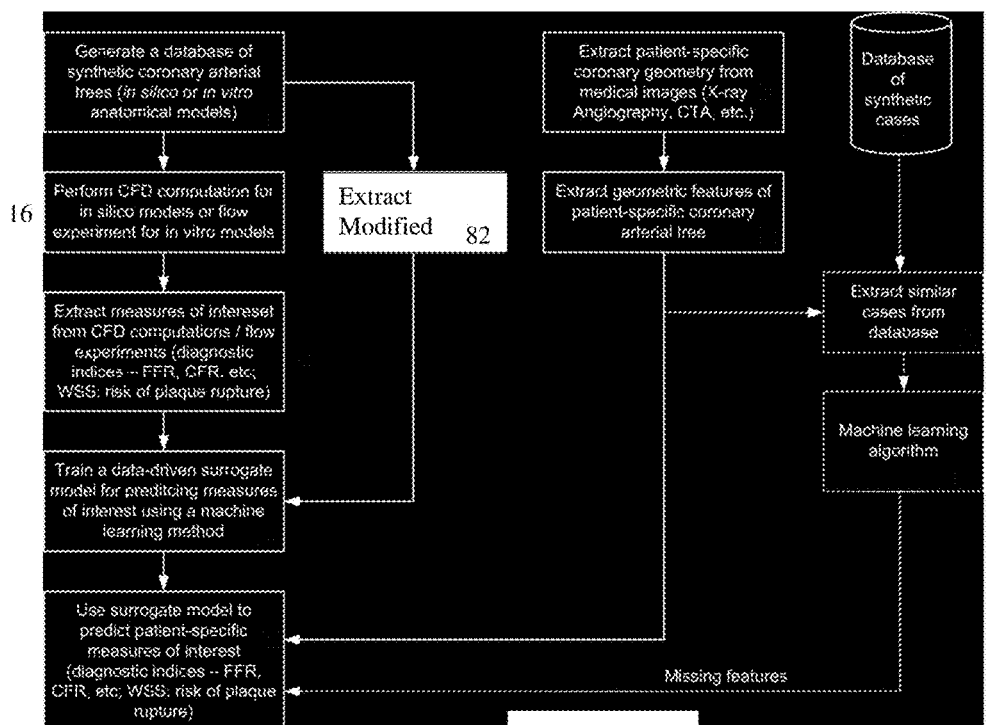
FIG. 43 is a flow chart of one embodiment of a method for hemodynamic determination in medical imaging using therapy modification.

Using the machine learning on synthetic data, another approach is provided. The feature values extracted and/or the geometry extracted are modified. FIG. 43 shows a method for modifying one or more features or geometry to account for therapy in order to decide which stenosis to treat. In acts 82 and 20, the extracted features values or the set of features are modified. In act 82, the feature values extracted from the synthetic geometries are modified to account for the therapy. During prediction, the extracted features in act 20 are modified to account for the therapy. One or both modifications are used. The classifier may be trained on many examples. The extracted features from the patient specific data are modified to emulate the effects of the planned therapy so that a resulting hemodynamic metric value is predicted. In another embodiment, the machine training incorporates likely modifications, creating related synthetic examples and corresponding calculated or measured metric values for more accurate training accounting for possible therapies.

For example, one approach modifies the features related to the ischemic contribution scores of the stenotic segments:

$$s = f_{41}(r(x))w_1 + f_{51}(r(x))w_1^2$$

where $f_{41}$ and $f_{51}$ are the modified versions of the operators $f_4$ and $f_5$. Furthermore, the ischemic weights of the branches containing the stenosis may also be modified, as a result of a different effect on the total contribution score of the corresponding branch or as a result of a different interaction between the branches. The modified features, corresponding values, and resulting hemodynamic ground truth are used to train the classifier. The modified features and corresponding values from patient-specific data are used to predict from the classifier. In one example, the modification is of features and values corresponding to the stenosis being modified to features and values corresponding to healthy vessel, to a stent, or to results from therapy where less flow restriction results.

This approach may be further extended in the sense that all possible post-stenting scenarios may be evaluated and a comprehensive analysis may be displayed to the user. The stenoses are ranked based on their effect on the hemodynamic metrics. A suggestion is given to the user regarding the stenoses that require treatment.

Figure 44:
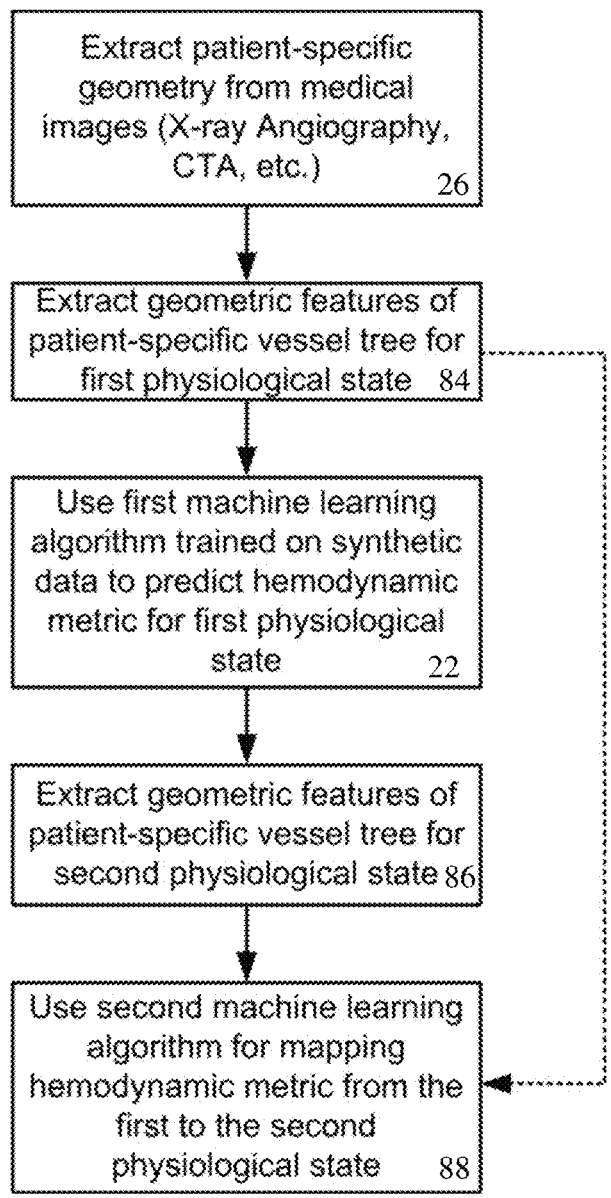
FIG. 44 is a flow chart of one embodiment of a method for hemodynamic determination in medical imaging from one physiological state to another.

FIG. 44 shows an embodiment of a method for addressing different physiological states. The physiological states may be any of rest, drug-induced hyperemia (e.g., intracoronary or intravenous), hyperemia generated by balloon inflation, exercise, post-treatment, or another state. Machine-learning is used to map from one physiological state to another. Any of the hemodynamic metrics may be predicted for any patient-specific state by adapting the features extracted from the synthetic geometries and by changing the flow conditions in the flow simulations and/or computations performed for the synthetic geometries. FIG. 44 represents a different approach.

A machine trained classifier is used to map the hemodynamic metric obtained for a certain physiological state of the patient to a different physiological state of the patient. A sequential machine learning based strategy is applied. The extracted features in act 84 are for a given state, so that the value of the hemodynamic metric is predicted for that state. In sequence, further features with or without some or all of the features used in act 84 are extracted in act 86. The features extracted are for a different physiological state. A second machine-learnt classifier is trained and used in act 88 to map the results from the first physiological state to the second physiological state. This second classifier algorithm may rely on any features, such as: geometric features specific to the first physiological state, geometric features specific to the second physiological state, and/or a hemodynamic metric predicted for the first physiological state. The geometric features specific to the second physiological state may be derived by modifying the constants and the operators used, such as in the computation of the ischemic weights and ischemic contribution scores.

Figure 45:
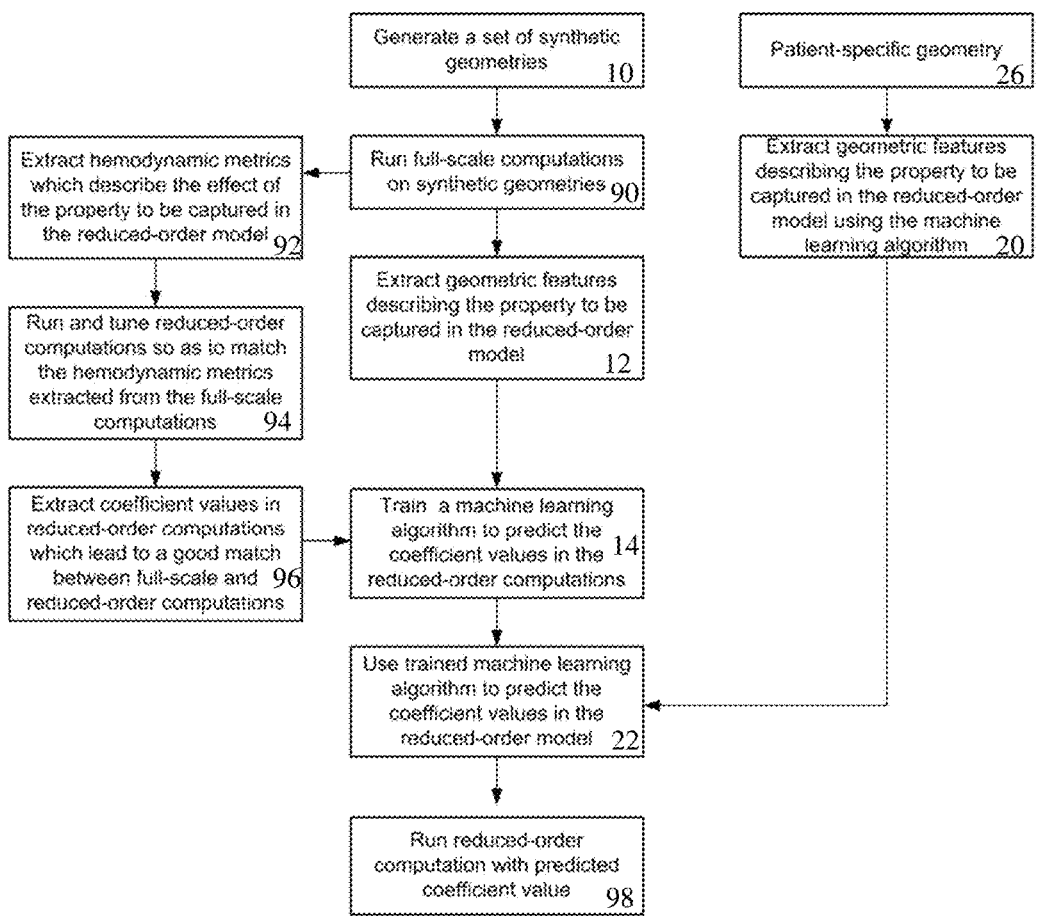
FIG. 45 is a flow chart of one embodiment of a method for hemodynamic determination in medical imaging using reduction in order of the modeling.

FIG. 45 shows another embodiment for improving reduced-order models using machine learning. Machine learning approaches may be used to improve reduced-order models. A full-scale (three-dimensional) blood flow model provides higher fidelity when computing blood flow compared to a reduced-order model. For example, the effect of vessel curvature is not captured in a one-dimensional blood flow model. Additional coefficients may be added in the reduced-order model to account for the effect of properties not captured by the reduced-order model.

To determine the values of these coefficients, a machine learning method may be used. A large number of full-scale geometries are first generated in act 10 and full-scale blood flow computations are performed for these geometries in act 90. A set of features describing the property that is not captured by the reduced-order model are extracted from the geometry, and a set of hemodynamic metrics (e.g. in case of curvature effect the tortuosity features described in a previous section may be used) are extracted from the computational results in act 92. Next, the reduced-order computations are performed in act 94, and the coefficients in the reduced-order model are adapted so as to match the hemodynamic metrics extracted from the full-scale model in act 96. The machine learning algorithm is trained in act 14 so as to be able to predict the values of the coefficients solely from the geometric features in act 22.

For example, an additional term may be added in the momentum conservation equation of the one-dimensional model so as to capture the effect of curvature on the viscous energy losses:

$$\frac{\partial q(x,t)}{\partial t} + \frac{\partial}{\partial x}\left(\alpha \frac{q^2(x,t)}{A(x,t)}\right) + \frac{A(x,t)}{\rho}\frac{\partial p(x,t)}{\partial x} = K_R \frac{q(x,t)}{A(x,t)} + c_{curvature}\frac{q(x,t)}{A(x,t)}$$

The coefficient to be estimated in this case would be $c_{curvature}$ while the hemodynamic metric extracted from the full-scale simulations is the pressure drop. Other coefficients may be used.

Various figures show methods for predicting a value for hemodynamic metric or performing other operations. The methods are implemented by a medical diagnostic imaging system, a review station, a workstation, a computer, a picture and archiving and communications system (PACS) station, a server, combinations thereof, or other device for image processing medical diagnostic data. Different devices may be used for training from examples in a database than for predicting. In one embodiment, the computer for training is described below with respect to FIG. 47. In another embodiment, the system of FIG. 47 predicts with a machine-trained classifier. Other systems may be used for either or both of training and prediction. A network may be used for providing input, distributed processing, outputting results, or other communications. A medical scanner provides scan data representing a patient. The scan data is image data or processed data.

The methods are implemented in the order shown or described or a different order. Additional, different, or fewer acts may be performed. For example, the acts related to prediction are provided without the acts for training. As another example, the acts for training are provided without the acts for prediction.

The acts for prediction may be performed in real-time, such as during a surgical procedure, during therapy planning, or during diagnosis by a medical professional. Performing during user interaction allows for more versatile diagnosis and/or planning. The hemodynamic metric value may be predicted in less than one minute for real-time performance. In other embodiments, the acts are performed not in real-time, such a serving results from a remote sever after a delay of minutes, hours, or days.

Since a machine-learnt classifier is used for predicting the hemodynamic metric value, the prediction may occur more rapidly than with computational flow dynamics. To show this difference, FFR may be analyzed.

FFR is an invasively measured functional parameter used to characterize the hemodynamic significance of a coronary artery stenosis. FFR is defined as the ratio of cycle-averaged pressure distal to the stenosis to the cycle-averaged aortic pressure. Over the years, multiple clinical trials have shown that FFR-guided stenting, clinically referred to as Percutaneous Coronary Intervention PCI, is superior to angiography-guided PCI, both in terms of long-term clinical outcomes, decrease in unnecessary revascularization, and cost effectiveness. Although strong clinical data now exists showing the superiority of FFR-based decision making for coronary stenosis treatment, the use of FFR is still relatively uncommon. The vast majority of coronary diagnoses are still based on pure anatomical information observed in medical images. This has partly been attributed to the requirement of inducing hyperemia, a condition which increases the blood flow before measuring FFR.

Blood-flow computations, performed using computational fluid dynamics, when used in conjunction with patient-specific anatomical models extracted from medical images, have been proposed for diagnosis, risk stratification, and surgical planning. CFD-based blood flow modeling approaches have been recently applied for evaluating coronary arterial hemodynamics, and estimating FFR. Studies have mainly focused on two types of medical image data: computer tomography angiography (CTA) and X-ray coronary angiography (XA). In case of CTA, blood flow characteristics are computed in the entire coronary arterial geometry (i.e., left and right coronary artery). Two different approaches may be used: full-order (3D) blood flow modeling where processing time varies between 2 and 6 hours, when being performed off-site on supercomputers or reduced-order blood flow modeling where processing time requires 10-12 minutes, when being performed on-site on a workstation. In the case of XA, since the coronary geometry may only be partially reconstructed, blood flow characteristics are computed for a subset of arterial segments. Previous studies reported a processing time which varied between 5 minutes and 24 hours. Since XA is invasive, the blood flow computation should ideally be performed during the procedure, in real-time or near real-time, so as to enable an immediate diagnosis and guide the patient treatment.

These approaches yield good results as compared with invasively measured FFR. Importantly, the CFD-based estimation of FFR is able to better discriminate between hemodynamically significant and non-significant coronary artery lesions than the pure anatomical evaluation, when using invasively measured FFR as gold standard.

Figure 46:
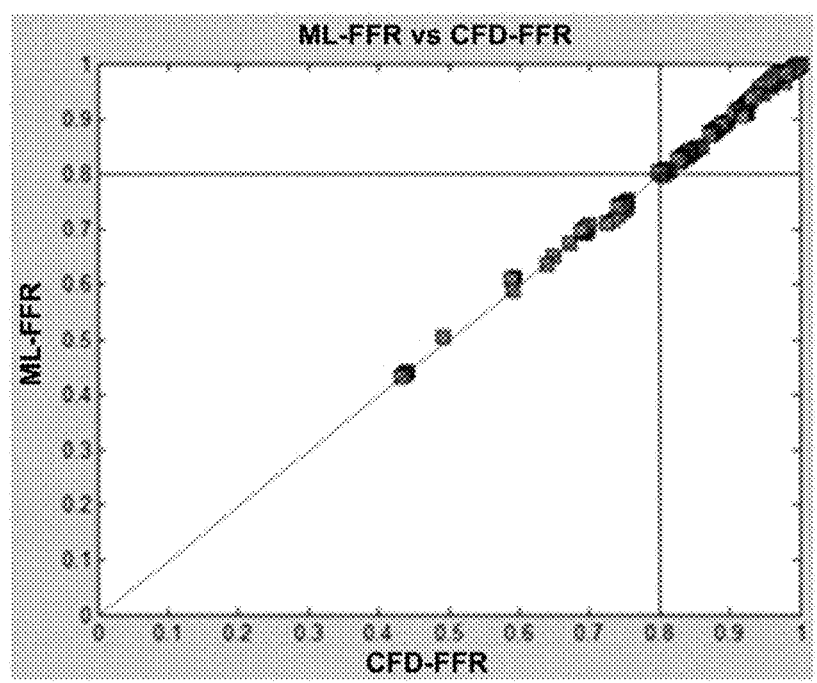
FIG. 46 shows an example comparison of machine-learnt as opposed to computational fluid dynamics computation of a hemodynamic metric.

A machine-learnt classifier is trained on features extracted from synthetic coronary geometries and on the hemodynamic metric of interest FFR, which is computed using a blood flow modeling (CFD) approach. In a preliminary implementation of this set-up, the machine learning-based FFR predictor produces results on patient-specific data which highly correlate with CFD based results for the same data (e.g., correlation: 0.9973). FIG. 46 shows the correlation between the two approaches.

Moreover, the machine learning-based approach enables a near real-time evaluation of coronary hemodynamic indices, requiring a total of 3-7 seconds for feature extraction and prediction on a regular desktop computer (Intel i7 8 cores, 3.4 GhZ, 8 GB RAM). Hence, the proposed approach is at least two orders of magnitude faster than reduced-order blood flow modeling approaches and at least 3 orders of magnitude faster than full-order blood flow modeling approaches using CFD. Real-time computation of FFR is provided on a standard radiology post-processing workstation without the need to transfer data offsite or wait for a long time to assess the results.

Given the advent of Coronary CTA in the emergency department, quick turn-around time for accurate diagnosis (e.g., rule-in or rule-out significant coronary disease) is key to improving the overall outcome and reducing the costs. The clinician may perform changes in the input data (e.g. severity of stenosis), motivated by the uncertainty in the input data, and reevaluate the coronary lesions in real-time. Furthermore, treatment planning may also be performed in near real-time: one or more lesions, marked by the user or chosen automatically, may be virtually treated (e.g. virtual stent placement), and the remaining lesions may be reevaluated.

Instead of using a hemodynamic quantity as the ground-truth, other metrics may be used as the ground-truth. As a result of the hemodynamic computations, a label may be attached to each location along the centerlines. The labels may be of any resolution, such as two types 'significant' and 'non-significant', referring to the fact that the upstream lesions are hemodynamically significant or not. Multiple labels may be used describing whether the lesion has no effect on the circulation, a mild effect, an intermediate effect, a severe or a very severe effect, or other effect. Furthermore, the labels may be based on a perfusion analysis that is performed in junction with the hemodynamic computations. A perfusion territory may be associated with each branch and labels of the type 'Perfusion defect' or 'No perfusion defect' may be used as ground truth during the training phase.

In another embodiment, the ground truth may be given by the change in luminal radiological attenuation. This approach may be used when synthetic medical images are used during the training phase, but may also be applied if contrast agent propagation analyses are performed for the synthetic geometries. The change in luminal radiological attenuation may be described by the change per 10 mm or other length of coronary artery, and then a linear regression coefficient between intraluminal radiologic attenuation and length from ostium may be computed for use as ground truth.

The ground truth may be the outcome from virtual percutaneous coronary intervention (PCI). In one embodiment, the system performs virtual PCI on each created or detected stenosis. The outcome is computed (e.g., in terms of FFR, or percentage perfusion to the downstream districts compared to the healthy case) and each lesion is graded based on contribution to the perfusion defect. The ground truth is then a measure of healthy perfusion after virtual PCI, for each location along the centerline.

Multiple optimization criteria (i.e. cost function that penalizes the mismatch between the prediction and the ground-truth) may be considered. One or more of the following metrics: PPV, NPV, specificity, sensitivity, diagnostic accuracy, and correlation may be maximized. Any combinations of these metric may also be used. For example, the specificity is maximized while keeping sensitivity less than 90%. The cost functions may be described in a weighted fashion using two cutoff points defining a range of acceptable FFR. For example, $\min \|FFR_{ML} - FFR_{cFD}\|$ over all ($FFR_{CFD} < x$ or $FFR_{CFD} > y$). In a clinical setting, the lower and upper cutoff points for ML-FFR may be different from an 0.8 cutoff value prescribed for invasive FFR.

Additionally, a cost function may be used for which different weights may be attached to different intervals of values of the ground-truth quantity. To achieve high classification accuracy, the values closer to the clinical cut-off point may have a larger weight than the values further away from the cut-off (e.g., in case of FFR, the interval 0.7-0.9 may have a larger weight than value outside of this range). Furthermore, additional constraints in terms of minimum and maximum values may be introduced that reflect the maximum variation of the quantities in clinical practice (e.g. FFR values lie between 0 and 1 in clinical practice). Any of these approaches may be applied for the training of any machine learning predictor, irrespective of whether the predictor being trained is the only predictor used in the application or if sequential machine learning predictors are applied.

Figure 47:
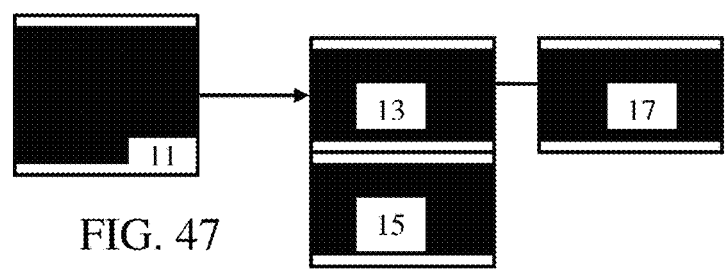
FIG. 47 is a block diagram of one embodiment of a system for hemodynamic determination in medical imaging.

FIG. 47 shows a system for hemodynamic determination in medical imaging. The system includes a medical imaging system 11, a processor 13, a memory 15, and a display 16. The processor 13 and the memory 15 are shown separate from the medical imaging system 11, such associated with being a computer or workstation apart from the medical imaging system 11. In other embodiments, the processor 13 and/or memory 15 are part of the medical imaging system 11. In alternative embodiments, the system is a workstation, computer, or server for hemodynamic determination in medical imaging. For example, the medical imaging system 11 is provided for acquiring data representing a volume, and a separate database, server, workstation, and/or computer is provided for extracting geometry and/or features and applying a classifier to predict one or more hemodynamic metrics. Additional, different, or fewer components may be used.

The system is used for application. In alternative embodiments, the system is used for training and/or generation of the examples in the database.

The computing components, devices, or machines of the system, such as the medical imaging system 11 and/or the processor 13 are configured by hardware, software, and/or design to perform calculations or other acts. The computing components operate independently or in conjunction with each other to perform any given act, such as the acts of any of the methods described above. The act is performed by one of the computer components, another of the computing components, or a combination of the computing components. Other components may be used or controlled by the computing components to scan or perform other functions.

The medical imaging system 11 is any now known or later developed modality for scanning a patient. The medical imaging system 11 scans the patient for a vessel region. For example, a C-arm x-ray system (e.g., DynaCT from Siemens), CT like system, or CT system is used. Other modalities include MR, x-ray, angiography, fluoroscopy, PET, SPECT, or ultrasound. The medical imaging system 11 is configured to acquire the medical imaging data representing one or more vessels. The data is acquired by scanning the patient using transmission by the scanner and/or by receiving signals from the patient. The type or mode of scanning may result in receiving data of just the vessel. Alternatively, data of a volume region is received and the vessel information is segmented from information of other anatomy.

The memory 15 is a buffer, cache, RAM, removable media, hard drive, magnetic, optical, database, or other now known or later developed memory. The memory 15 is a single device or group of two or more devices. The memory 15 is within the system 11, part of a computer with the processor 13, or is outside or remote from other components.

The memory 15 is configured to store medical scan data, extracted geometry of the vessel tree, extracted features from the medical scan data, geometry or other source, examples (e.g., geometry from synthetic data, extracted features from the geometry, and ground truth hemodynamic metric value), and/or other information. For example, the memory 15 stores ischemic values, such as a weight and contribution.

The memory 15 is additionally or alternatively a non-transitory computer readable storage medium with processing instructions. The memory 15 stores data representing instructions executable by the programmed processor 13 for hemodynamic metric estimation in medical imaging. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The processor 13 is a general processor, digital signal processor, three-dimensional data processor, graphics processing unit, application specific integrated circuit, field programmable gate array, digital circuit, analog circuit, combinations thereof, or other now known or later developed device for processing data. The processor 13 is a single device, a plurality of devices, or a network. For more than one device, parallel or sequential division of processing may be used. Different devices making up the processor 13 may perform different functions, such as extracting geometry or feature values by one device and computation of flow quantities by another device. In one embodiment, the processor 13 is a control processor or other processor of the medical imaging system 11. The processor 13 operates pursuant to stored instructions to perform various acts described herein.

The processor 13 is configured to extract geometry, extract feature values, interact with the user in extraction, apply features to a machine-trained predictor, and generate an image or other output. In embodiment, the processor 13 is configured to modify one or more features or feature values to emulate a geometry being in a therapeutically corrected state from an abnormal state. By modifying the features, the hemodynamic operation of the vessel after therapy may be predicted. The processor 13 is configured to apply the features, including any modified features or features with uncertainty, to a machine-trained predictor trained with training data of examples of vessels. The machine-trained predictor may be trained from training examples in the therapeutically corrected state for prediction of therapy results. For therapy planning, the application is repeated by the processor 13 multiple times for different modifications of the feature or features associated with different therapeutically corrected states. For uncertainty, the application is performed once where the predictor is trained on uncertainty information or is performed multiple times to determine a distribution of the hemodynamic metric values given the uncertainty of the input feature value.

The processor 13 is configured to output a prediction. By application of the input feature vector to the machine-learnt predictor, the predictor outputs a prediction or estimate of the hemodynamic variable, such as FFR. The output prediction is in the form of text, graph, color coding, or other representation.

The display 16 is a CRT, LCD, plasma, projector, printer, or other output device for showing an image. The display 16 displays the quantity or quantities output by the processor 13. The quantities may be displayed in a chart, graph, and/or on an image. The display 16 is configured by display values to indicate the value of the hemodynamic metric. The value may be displayed in association with the geometry, features, and/or an image. In one embodiment, the value of the hemodynamic metric is displayed with an image representing a therapeutically corrected state. In an additional or alternative embodiment, the uncertainty associated with the value of the metric is displayed, such as displaying the value as an uncertainty interval.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for hemodynamic determination in medical imaging, the method comprising:
   acquiring medical scan data representing an anatomical structure of a patient;
   extracting a set of features from the medical scan data;
   inputting, by a processor, the features to a machine-trained classifier, the machine trained classifier trained only from synthetic data not specific to any patients; and
   outputting, by the processor with application of the machine-trained classifier to the features, a hemodynamic metric.

2. The method of claim 1 wherein acquiring comprises acquiring angiography data.

3. The method of claim 1 wherein acquiring comprises acquiring with the medical scan data comprising a two or three-dimensional representation of the anatomical structure.

4. The method of claim 1 wherein extracting the set of the features comprises:
   extracting geometrical features of the anatomical structure; and
   extracting the features of one or more abnormalities of the anatomical structure.

5. The method of claim 1 wherein extracting the set of the features comprises extracting functional features representing operation of the anatomical structure, wherein the machine-trained classifier is trained from virtual representations of the operation of the anatomical structure.

6. The method of claim 1 wherein extracting the set of the features comprises extracting an ischemic weight and an ischemic contribution score, the ischemic contribution score being a function of the ischemic weight.

7. The method of claim 6 wherein extracting the ischemic weight comprises computing branch ischemic weights as a function of a global ischemic weight.

8. The method of claim 6 wherein extracting the ischemic contribution score comprises computing the ischemic contribution score as a function of the ischemic weight and a radius.

9. The method of claim 1 wherein extracting the set of the features comprises extracting branch interaction features.

10. The method of claim 1 wherein inputting comprises inputting to the machine-trained classifier trained only from the synthetic data, the synthetic data comprising an in vitro model with a ground truth of the hemodynamic metric measured form the in vitro model.

11. The method of claim 1 wherein inputting comprises inputting to the machine-trained classifier trained only from the synthetic data, the synthetic data comprising an in silico model with a ground truth of the hemodynamic metric computed with computation fluid dynamics.

12. The method of claim 1 wherein inputting comprises inputting a sub-set of the set of features, the sub-set for a sub-part of the anatomical structure, and wherein outputting comprises outputting the hemodynamic metric for the sub-part of the anatomical structure; and
   further comprising subsequently repeating the inputting and outputting for remaining features of the set for another part of the anatomical structure.

13. The method of claim 1 wherein outputting comprises outputting a value of the hemodynamic metric on a display with an image of the anatomical structure generated from the medical scan data.

14. The method of claim 1 further comprising predicting another value of the hemodynamic metric with another machine-trained classifier using at least one of the different values and patient characteristics as input features.

15. The method of claim 1 wherein inputting comprises inputting to the machine-trained classifier trained from the synthetic data, the synthetic data comprising examples generated by regular variation of an in vitro model, in silico model, or both in vitro and in silico models.

16. The method of claim 1 wherein outputting the hemodynamic metric comprises outputting fractional flow reserve.

17. The method of claim 1 wherein outputting the hemodynamic metric comprises outputting wall stress.

18. A method for hemodynamic determination in medical imaging, the method comprising:
generating a plurality of examples of anatomical arrangements not representing any particular patient with computer modeling in silico, physical modeling in vitro, or both computer modeling in silico and physical modeling in vitro;
storing a value for a flow characteristic for each of the examples of the anatomical arrangements; and
training, with machine learning, using the stored value for the flow characteristic for each of the examples of the anatomical arrangements, a classifier for predicting the flow characteristics for different anatomical arrangements.

19. The method of claim 18 wherein generating comprises perturbing the computer modeling, physical modeling, or both in a systematic pattern.

20. A system for hemodynamic determination in medical imaging, the system comprising:
a scanner configured to scan a vessel of a patient;
a memory configured to store a plurality of features of the vessel of the patient, the features determined from the scan of the vessel;
a processor configured to apply the features to a machine-trained predictor trained with training data of synthetic examples of vessels not specific to any particular patient, and to output a prediction of a value of a hemodynamic variable based on the application of the features to the machine-trained predictor; and
a display configured to indicate the value of the hemodynamic variable.

21. The system of claim 20 wherein one of the features comprises an ischemic value and wherein the application is repeated multiple times for different modifications of the ischemic value associated with different therapeutically corrected states.

22. A system for hemodynamic determination in medical imaging, the system comprising:
a scanner configured to scan a vessel of a patient;
a memory configured to store a plurality of features of the vessel of the patient, the features determined from the scan of the vessel;
a processor configured to modify a first feature of the features from an abnormal state to a therapeutically corrected state, to apply the features including the first feature as modified to a machine-trained predictor trained with training data of examples of vessels in the therapeutically corrected state, and to output a prediction of a value of a hemodynamic variable based on the application of the features to the machine-trained predictor; and
a display configured to indicate the value of the hemodynamic variable in association with the therapeutically corrected state.

23. The system of claim 22 wherein the first feature comprises an ischemic value and wherein the application is repeated multiple times for different modifications of the first feature associated with different therapeutically corrected states.

* * * * *